(12) United States Patent
Marcus et al.

(10) Patent No.: US 10,269,525 B2
(45) Date of Patent: Apr. 23, 2019

(54) MEANS OF INTRODUCING AN ANALYTE INTO LIQUID SAMPLING ATMOSPHERIC PRESSURE GLOW DISCHARGE

(71) Applicants: CLEMSON UNIVERSITY, Clemson, SC (US); Lawrence Berkeley National Laboratory, Berkeley, CA (US); Pacific Northwest National Laboratory, Richland, WA (US)

(72) Inventors: R. Kenneth Marcus, Clemson, SC (US); Charles Derrick Quarles, Jr., San Jose, CA (US); Richard E. Russo, Berkeley, CA (US); David W. Koppenaal, Richland, WA (US); Charles J. Barinaga, Richland, WA (US); Anthony J. Carado, Richland, WA (US)

(73) Assignees: Clemson University Research Foundation, Clemson, SC (US); Battelle Memorial Institute on behalf of Pacific Northwest National Laboratory, Richland, WA (US); The Regents of the University of California—Lawrence Berkeley National Laboratory, Berkeley, CA (US)

(*) Notice: Subject to any disclaimer, the term of this patent is extended or adjusted under 35 U.S.C. 154(b) by 63 days.

(21) Appl. No.: 15/359,969

(22) Filed: Nov. 23, 2016

(65) Prior Publication Data
US 2017/0162358 A1    Jun. 8, 2017

Related U.S. Application Data

(63) Continuation of application No. 14/171,981, filed on Feb. 4, 2014, now Pat. No. 9,536,725.

(Continued)

(51) Int. Cl.
*H01J 27/02* (2006.01)
*H01J 49/10* (2006.01)
(Continued)

(52) U.S. Cl.
CPC ............. *H01J 27/022* (2013.01); *G01J 3/443* (2013.01); *H01J 27/16* (2013.01); *H01J 49/105* (2013.01); *H01J 49/145* (2013.01); *H01J 49/165* (2013.01)

(58) Field of Classification Search
CPC ...... H01J 49/105; H01J 49/165; H01J 49/145; H01J 27/16; G01J 27/022; G01J 3/443
See application file for complete search history.

(56) References Cited

U.S. PATENT DOCUMENTS

| 3,588,601 A | 6/1971 | Yamasaki |
| 3,626,234 A | 12/1971 | Grimm |

(Continued)

FOREIGN PATENT DOCUMENTS

| CA | 2049876 | 3/1992 |
| FR | 2616545 | 12/1988 |
| JP | 0197873 | 10/1985 |

OTHER PUBLICATIONS

Carado et al., "Femtosecond laser ablation particle introduction to a liquid sampling—atmospheric pressure glow dishcharge ionization source," *J. Anal. At. Spectrom.*, 2012 (27) pp. 385-389.

(Continued)

*Primary Examiner* — Michael P LaPage
(74) *Attorney, Agent, or Firm* — Dority & Manning, PA

(57) ABSTRACT

A liquid sampling, atmospheric pressure, glow discharge (LS-APGD) device as well as systems that incorporate the device and methods for using the device and systems are described. The LS-APGD includes a hollow capillary for delivering an electrolyte solution to a glow discharge space.

(Continued)

The device also includes a counter electrode in the form of a second hollow capillary that can deliver the analyte into the glow discharge space. A voltage across the electrolyte solution and the counter electrode creates the microplasma within the glow discharge space that interacts with the analyte to move it to a higher energy state (vaporization, excitation, and/or ionization of the analyte).

11 Claims, 8 Drawing Sheets

Related U.S. Application Data

(60) Provisional application No. 61/760,824, filed on Feb. 5, 2013.

(51) Int. Cl.
  G01J 3/443 (2006.01)
  H01J 27/16 (2006.01)
  H01J 49/14 (2006.01)
  H01J 49/16 (2006.01)

(56) References Cited

U.S. PATENT DOCUMENTS

| | | | |
|---|---|---|---|
| 3,876,305 A | 4/1975 | Gough et al. | |
| 4,128,336 A | 12/1978 | Butler | |
| 4,167,667 A | 9/1979 | Hall et al. | |
| 4,368,850 A | 1/1983 | Szekely | |
| 4,381,664 A | 5/1983 | Clark et al. | |
| 4,383,171 A | 5/1983 | Sinha et al. | |
| 4,501,965 A | 2/1985 | Douglas | |
| 4,634,867 A | 1/1987 | Ottley et al. | |
| 4,687,929 A | 8/1987 | Browner et al. | |
| 4,762,995 A | 8/1988 | Browner et al. | |
| 4,795,588 A | 1/1989 | P4et et al. | |
| 1,808,827 A | 2/1989 | Woollam | |
| 4,812,040 A | 3/1989 | Marcus et al. | |
| 4,817,449 A | 4/1989 | Tyrant | |
| 4,824,249 A | 4/1989 | Lucas et al. | |
| 4,849,628 A | 7/1989 | McLuckey et al. | |
| 4,853,539 A | 8/1989 | Hall et al. | |
| 4,872,786 A | 10/1989 | Braden | |
| 4,883,958 A | 11/1989 | Vestal | |
| 4,912,324 A | 3/1990 | Clark et al. | |
| 4,924,097 A | 5/1990 | Browner et al. | |
| 4,928,537 A | 5/1990 | Liu et al. | |
| 5,006,706 A | 4/1991 | Marcus | |
| 5,086,226 A | 2/1992 | Marcus | |
| 5,096,615 A | 3/1992 | Prescott et al. | |
| 5,105,123 A | 4/1992 | Ballou | |
| 5,175,433 A | 12/1992 | Browner et al. | |
| 5,184,016 A | 2/1993 | Ronan et al. | |
| 5,192,865 A | 3/1993 | Zhu | |
| 5,266,192 A | 11/1993 | Ligon et al. | |
| 5,319,575 A | 6/1994 | Lilienfeld | |
| 5,325,021 A | 6/1994 | Duckworth et al. | |
| 5,331,160 A | 7/1994 | Whitt | |
| 5,345,079 A | 9/1994 | French et al. | |
| 5,382,794 A | 1/1995 | Downey et al. | |
| 5,400,665 A | 3/1995 | Zhu et al. | |
| 5,408,315 A | 4/1995 | Mitchell et al. | |
| 5,410,918 A | 5/1995 | Zimmerman | |
| 5,412,975 A | 5/1995 | Raabe et al. | |
| 5,437,198 A | 8/1995 | John | |
| 5,500,369 A | 3/1996 | Kiplinger | |
| 5,565,677 A | 10/1996 | Wexler et al. | |
| 5,681,752 A | 10/1997 | Prather | |
| 5,896,196 A | 4/1999 | Pinnaduwage | |
| 5,998,215 A | 12/1999 | Prather et al. | |
| 6,050,574 A | 4/2000 | Olson et al. | |
| 6,465,776 B1 | 10/2002 | Moini et al. | |
| 6,566,652 B1 | 5/2003 | Kato | |
| 6,686,998 B2 | 2/2004 | Gianchandani et al. | |
| 6,750,449 B2 | 6/2004 | Marcus | |
| 6,852,969 B2 | 2/2005 | Marcus et al. | |
| 7,372,043 B2* | 5/2008 | Joyce | H01J 49/0422 250/281 |
| 7,375,319 B1 | 5/2008 | Willoughby | |
| 7,586,092 B1* | 9/2009 | Karpetsky | G01N 27/624 250/281 |
| 7,929,138 B1* | 4/2011 | Webb | G01N 21/67 356/313 |
| 9,536,725 B2 | 1/2017 | Marcus et al. | |
| 2002/0175278 A1* | 11/2002 | Whitehouse | H01J 49/0095 250/281 |
| 2003/0155502 A1* | 8/2003 | Grosshans | H01J 49/0095 250/282 |
| 2004/0017565 A1 | 1/2004 | Shimidzu | |
| 2005/0012038 A1 | 1/2005 | Marcus | |
| 2009/0294660 A1 | 12/2009 | Whitehouse | |
| 2012/0080592 A1 | 4/2012 | Wiseman | |

OTHER PUBLICATIONS

Coburn, et al; "Glow Discharge Mass Spectrometry Technique for Determining Elements Comp. Profiles in Solids," *Jnl. of Applied Physics* (Apr. 1974) vol. 45 #4, pp. 1779-1786.

Couch et al.; "Glow Discharge Spectra of Copper and Indium Above Aqueous Solutions," *Chemistry Division, National Bureau of Standards, Washington, D.C.*, pp. 628 and 629.

Cserfaivi et al; "Direct Solution Analysis by Glow Discharge: Electrolyte-Cathode Discharge Spectrometry," *Journal of Analytical Atomic Spectrometry*, Mar. 1994, vol. 9, pp. 346-349.

Cserfaivi et al; "Emission Studies on a Glow Discharge in Atmospheric Pressure Air Using Water as a Cathode," *J. Phys D. Appl. Phys.* 26 (1993) pp. 2184-2188.

Donohue et al; "Radio Frequency Cavity Ion Source in Solids Mass Spectrometry," *Analytical Chemistry*, vol. 47, #9, Aug. 1975, pp. 1528-1531.

Duckworth, et al; "RF Powered Glow Discharge Atomization/ Ionization Source for Solids Mass Spectrometry," *Analytical Chemistry*, vol. 61, No. 17, Sep. 1989, pp. 1879-1886.

Freemantle, "Downsizing Chemistry Chemical analysis and synthesis on microchips promise a variety of potential benefits," *C&EN London*. Feb. 22, 1999, pp. 27-36.

Henry, C; "Dust In The Wind," *Analytical Chemistry News & Features*, Jul. 1, 1998.

Kebarle, "A Brief Overview of the Present Status of the Mechanisms Involved in Electrospray Mass Spectrometry," *J. Mass Spectrom.* (2000)35, pp. 804-817.

Ketchell's, Niel; Ph.D. dissertation entitled, "An Investigation of DC and RF Sputtering Glow Discharges for the Mass Spectrometric Analysis of Solids from the University of Manchester," (1989).

Kim et al; "Development of Open-Air Type Electrolyte-as-Cathode Glow Discharge-Atomic Emission Spectrometry for Determination of Trace Metals in Water,"*Sectrochimica Acta Pari B*, (2000) 55 pp. 823-831.

Marcus et al; "Analysis of Geological Samples by Hollow Cathode Plume Atomic Emission Spectrometry," *Analytical Chemistry*, vol. 59, No. 19, Oct. 1987, pp. 2369-2373.

Mezei et al; Pressure Dependence of the Atmospheric Electrolyte Cathode Glow Discharge Spectrum, *Journal of Analytical Atomic Spectrometry* (1997), pp. 1203-1208.

Mezie et al; Rapid Communication the Gas Temperature in the Cathode Surface-Dark Space Boundary Layer of an Electrolyte Cathode Atmospheric Glow Discharge (ELCAD), *J. Phys. D: Appl. Phys.* 31 (1998) pp. L41-L42.

Park et al; "Fundamental Studies of Electrolyte-as-Cathode Glow Discharge-Atomic Emission Spectrometry for the Determination of Trace Metals in Flowing Water," *Spectrochimica Acta Part B*, 53 (1998), pp. 1167-1179.

Pittcon (R); Book of Abstracts, Mar. 1-5, 1998.

Quarles, Jr., et al; "Liquid sampling—atmospheric pressure glow discharge optical emission spectroscopy detection of laser ablation produced particles: A feasibility study,"*Spectrochimica Acta Part B*; 2012 (76) pp. 190-196.

(56) References Cited

OTHER PUBLICATIONS

Strange, et al; "Aqueous Sample Introduction Into A Glow Discharge Device Via A Particle Beam Interface," *Spectrochimica Acta*. vol. 46B, No. 4; pp. 517-426, 1991.

Wood, et al; "Time-Of-Flight Mass Spectrometry Methods For Real Time Analysis Of Individual Aerosol Particles," *Trends in Analyticai Chemistry*, vol. 17, No. 6, 1998.

Yokogawa Electric Corporation, "Technical Information, Model PT1000/CY2000 Particle Analyzer System," Mar. 1996.

You, et al.; "Nebulization And Analysis Characteristics Of A Particle Beam-Hollow Cathode Glow Discharge Atomic Emission Spectrometry System," *Journal Of Analytical Atomic Spectrometry*, Jul. 1996, vol. 11 (483-490).

You, et al.; "Studies Of Analyte Particle Transport In A Particle Beam-Hollow Cathode Atomic Emission Spectrometry System," *Journal of Analytical Atomic Spectrometry*, Aug. 1997, vol. 12 (807-815).

You, et al; "Analysis Of Organic Compounds By Particle Beam/ Hollow Cathode Atomic Emission Spectroscopy: Determinations Of Carbon And Hydrogen In Amino Acids," *Analytical Chemistry*, vol. 69, No. 17, Sep. 1, 1997.

You, et al; "Particle Beam Aqueous Sample Introduction For Hollow Cathode Atomic Emission Spectroscopy," *Analytical Chemistry*, vol. 66, No. 22, Nov. 15, 1994.

Takats Z, Wiseman JM, Gologan B, Cooks RG. Mass spectrometry sampling under ambient conditions with desorption electrospray ionization. Science. Oct. 15, 2004;306(5695):471-473.

Cody RB, Laramée JA, Durst HD, Versatile new ion source for the analysis of materials in open air under ambient conditions. Analytical chemistry. Apr. 15, 2005;77(8);2297-302.

Venter A, Nefliu M, Cooks RG. Ambient desorption ionization mass spectrometry, TrAC Trends in Analytical Chemistry. Apr. 30, 2008;27(4):284-290.

Harris GA, Galhena AS, Fernandez FM. Ambient sampling/ ioinzation mass spectrometry: applications and current trends. Analytical Chemistry. May 6, 2011;83(12):4508-4538.

Shelley JT, Wiley JS, Hieftje GM, Ultrasensitive ambient mass spectrometric analysis with a pin-to-capillary flowing atmospheric-pressure afterglow source. Analytical chemistry. Jul. 15, 2011;83(14);5741.

Albert A, Shelley JT, Engelhard C. Plasma-based ambient desorption/ ionization mass spectrometry: state-of-the-art in qualitative and quantitative analysis. Analytical and bioanalytical chemistry. Oct. 1, 2014:406(25):6111-6127.

Shelley JT, Hieftje GM. Ambient mass spectometry: Approaching the chemical analysis of things as they are. Journal of Analyticla Atomic Spectrometry. 2011:26(11):2153-2159.

Takats Z, Wiseman JM, Cooks RG. Ambient mass spectrometry using desorption electrospray ionization (DESI): instrumentation, mechanisms and applications in forensics, chemistry, and biology. Journal of Mass Spectrometry. Oct. 1, 2005;40(10):1261-1275.

Jones RW, Cody RB, McClelland JF. Differentiating writing inks using direct analysis in real time mass spectrometry. Journal of forensic sciences. Jul. 1, 2006;51(4):915-918.

Sampson JS, Muddiman DC. Atmospheric pressure infrared (10.6 μm) laser desorption electrospray ionization (IR-LDESI) coupled to a LTQ Fourier transform ion cyclotron resonance mass spectrometer. Rapid Communications in Mass Spectrometry. Jul. 15, 2009;23(13):1989-1992.

Li H, Smith BK, Mark L, Nemes P, Nazarian J, Vertes A. Ambient molecular imaging by laster ablation electrospray ionization mass spectrometry with ion mobility seperation. International Journal of Mass Spectrometry, Feb. 1, 2015;377:681-689.

Shelley JT, Ray SJ, Hieftje GM. Laser ablation coupled to a flowing atmospheric pressure afterglow for ambient mass spectral imaging. Analytical chemistry. Oct. 1, 2008;80(21):8308-8313.

Davis WC, Marcus RK. An atmospheric pressure glow discharge optical emission source for the direct sampling of liquid mediaPresented at the 2001 European Winter Conference on Plasma Spectrochemistry, Lillehammer, Norway, Feb. 4-8, 2001. Journal of Analytical Atomic Spectrometry. 2001;16(9):931-937.

Venzie JL, Marcus RK. Effects of easily ionizable elements on the liquid sampling—atmospheric pressure glow discharge. Spectrochimica Acta Part B: Atomic Spectroscopy. Jun. 30, 2006;61(6):715-721.

Manard BT, Gonzalez JJ, Sarkar A, Dong M. Chirinos J, Mao X, Russo RE, Marcus RK. Liquid sampling—atmospheric pressure glow discharge as a secondary excitation source: assessment of plasma characteristics. Spectrochimica Acta Part B: Atomic Spectroscopy, May 1, 2014:94:39-47.

Manard BT, Konegger-Kappel S, Gonzalez JJ, Chirinos J. Dong M, Mao X, Marcus RK, Russo RE. Liquid Sampling—Atmospheric Pressure Glow Discharge as a Secondary Excitation Source for Laser Ablation-Generated Aerosols: Parametric Dependence and Robustness to Particle Loading. Applied spectroscopy. Jan. 2015;69(1):58-66.

Marcus RK, Quarles Jr CD, Barinaga CJ, Carado AJ, Koppenaal DW. Liquid sampling—atmospheric pressure glow discharge ionization source for elemental mass spectrometry. Analytical chemistry. Feb. 28, 2011:83(7):2425-2429.

Zhang LX, Manard BT, Kappel SK, Marcus RK. Evaluation of the operating parameters of the liquid sampling—atmospheric pressure glow discharge (LS-APGD) ionization source for elemental mass spectrometry. Analytical and bioanalytical chemistry. Nov. 1, 2014:406(29):7497-509.

Konegger-Kappel S, Manard BT, Zhang LX, Konegger T, Marcus RK. Liquid sampling—atmospheric pressure glow discharge excitation of atomic and ionic species. Journal of Analytical Atomic Spectrometry; 2015;30(1):285-295.

Marcus RK, Burdette CQ, Manard BT, Zhang LX. Ambient desorption/ ionization mass spectrometry using a liquid sampling—atmospheric glow discharge (LS-APGD) ionization source. Analytical and bioanalytical chemistry. Oct. 1, 2013;405(25):8171-8184.

Zhang LX, Manard BT, Powell BA, Marcus RK, Preliminary Assessment of Potential for Metal-Ligand Speciation in Aqueous Solutions via the Liquid Sampling—Atmospheric Pressure Glow Discharge (LS-APGD) Ionization Source: Uranyl Acetate. Analytical chemistry. Jul. 2, 2015;87(14):7218-7225.

Harris GA, Hostetler DM, Hampton CY, Fernández FM. Comparision of the internal energy deposition of direct analysis in real time and electrospray ionization time-of-flight mass spectrometry. Journal of the American Society for Mass Spectrometry. May 31, 2010,21(5):855-863.

Salter TL, Gilmore IS, Bowfield A, Olabanji OT, Bradley JW. Ambient surface mass spectrometry using plasma-assisted desorption ionization: effects and optimization of analytical parameters for signal intensities of molecules and polymers. Analytical chemistry. Jan. 18, 2013;85(3):1675-1682.

Weston DJ. Ambient ionization mass spectrometry: current understanding of mechanistic theory; analytical performance and application areas. Analyst. 2010;135(4):661-668.

Marcus RK, Davis WC. An atmospheric pressure glow discharge optical emission source for the direct sampling of liquid media. Analytical chemistry. Jul. 1, 2001;73(13):2903-2910.

\* cited by examiner

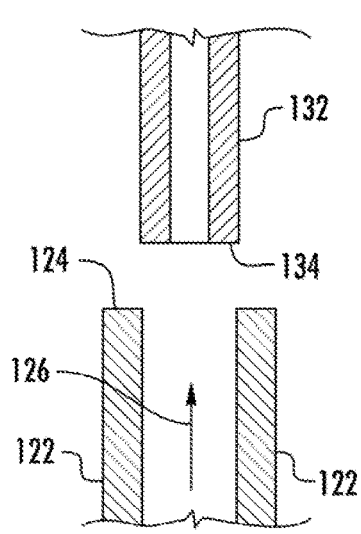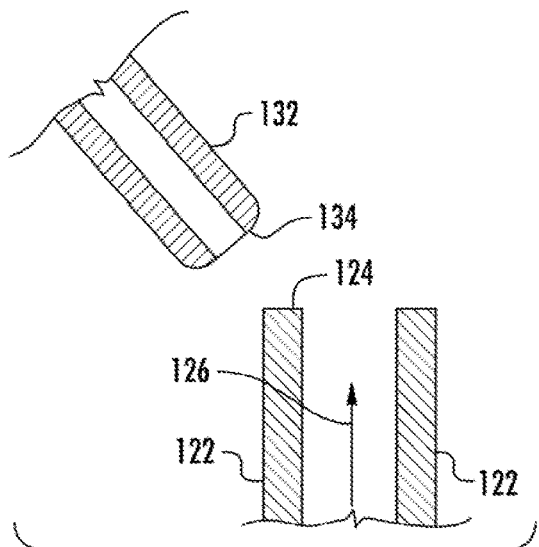
FIG. 5A  FIG. 5B
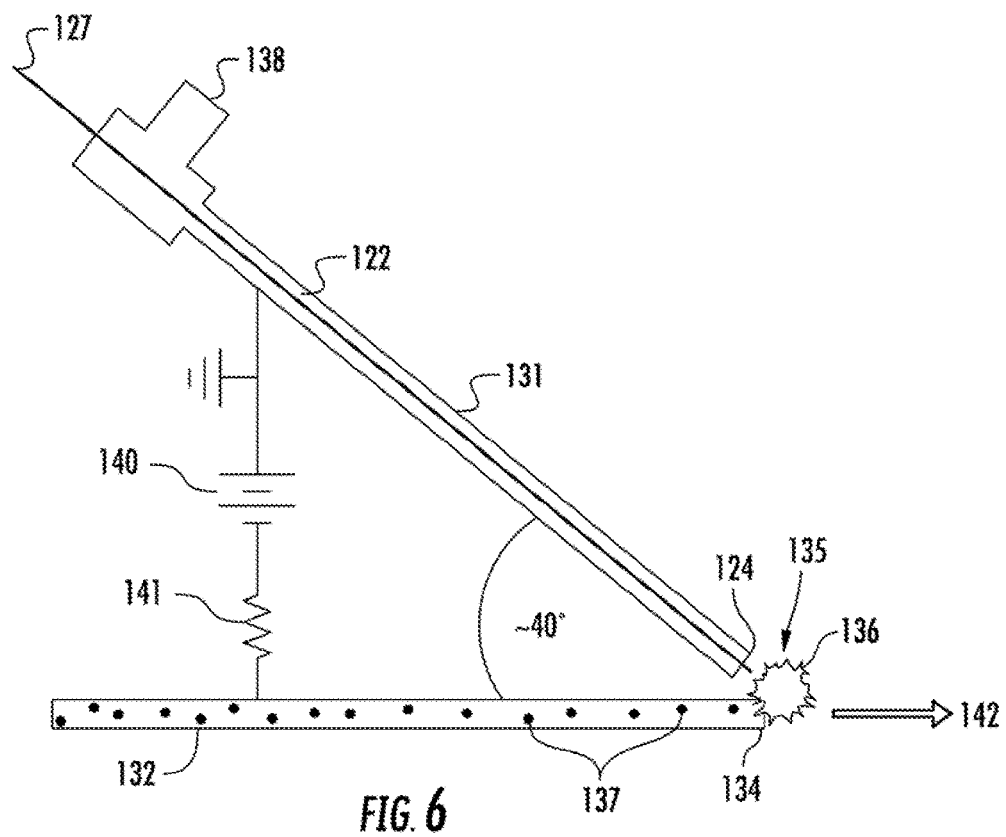
FIG. 6

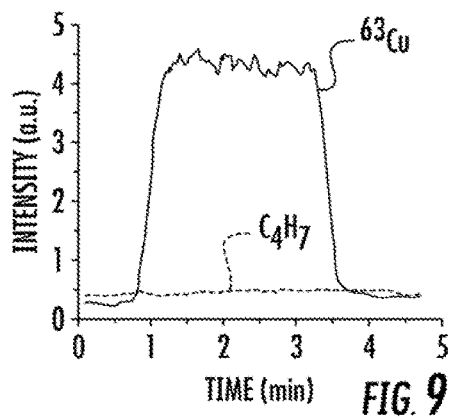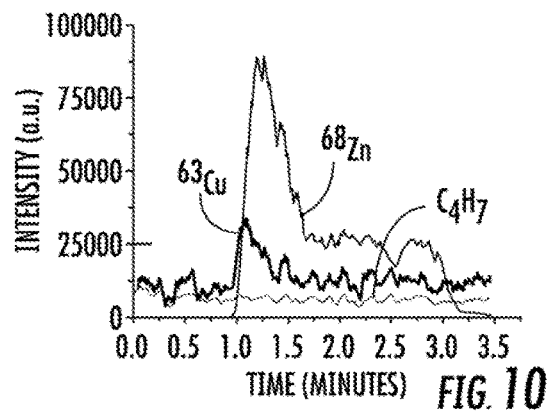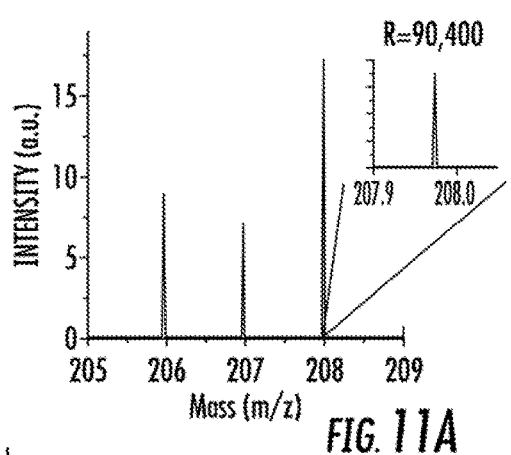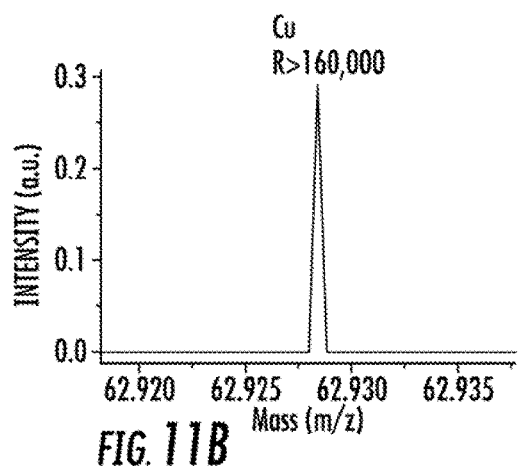
FIG. 11
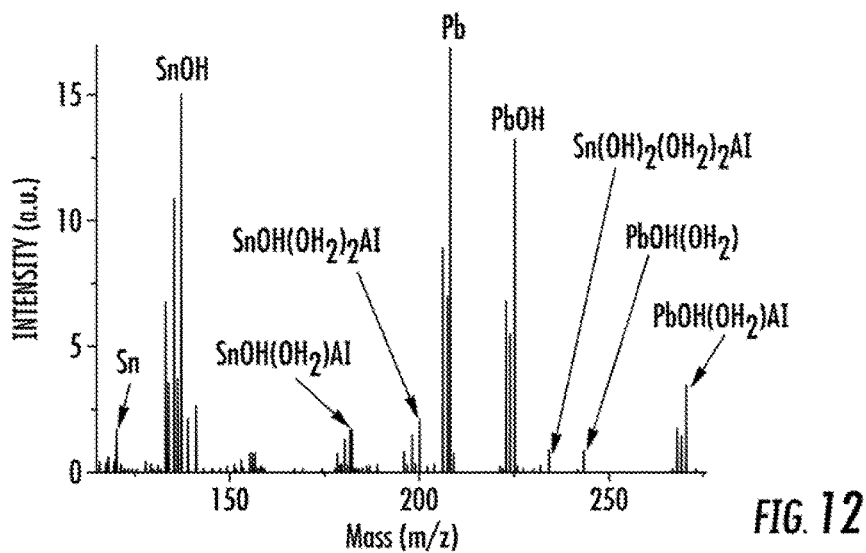

MEANS OF INTRODUCING AN ANALYTE INTO LIQUID SAMPLING ATMOSPHERIC PRESSURE GLOW DISCHARGE

CROSS REFERENCE TO RELATED APPLICATION

The present application is a continuation application of U.S. patent application Ser. No. 14/171,981 having a filing date of Feb. 4, 2014, which claims filing benefit of U.S. Provisional Patent Application Ser. No. 61/760,824 having a filing date of Feb. 5, 2013, which is incorporated herein in its entirety.

GOVERNMENT SUPPORT CLAUSE

This invention was made with government support under grant #DE-AC02-05CH11231 awarded by the Department of Energy and grant #DE-AC06-76RL01830 awarded by the Department of Energy and under grant #HDTRA1-14-1-0010 awarded by The Department of Defense, Defense Threat Reduction Agency. The government has certain rights in the invention.

BACKGROUND

The inductively coupled plasma (ICP) has been a standard excitation/ionization source for the analytical techniques of optical emission spectroscopy (OES) and elemental mass spectrometry (MS) for many years. Unfortunately, the general trend toward more compact and portable spectrochemical sources has been slower to reach elemental (atomic) spectrometry than other fields, largely because the ICP source has remained the workhorse of the field. In addition to their size, ICP sources typically consume large amounts of gas and sample solution.

The liquid sampling, atmospheric pressure, glow discharge (LS-APGD) is a low power, small footprint source that has been used in analytical techniques such as optical emission spectroscopy and mass spectrometry (see, e.g., U.S. Pat. Nos. 6,852,969, 6,750,449, 5,325,021, 5,086,226, and 5,006,706, all of which are incorporated herein by reference). The microplasma of these methods operates at power densities of about 10 W/mm$^3$, much higher than the typically-cited value of about 0.1 W/mm$^3$ for ICP. LS-APGD was originally developed for applications in metal speciation, being operable at low solution flow rates (<400 µL/min) and employing an electrolytic solution (5% acid/salt) as the mobile phase. In the direct solution analysis mode, heat is generated as current flows across the air/liquid interface and causes evaporation, eventually culminating in excitation of the analyte species passing through the microplasma. For quantitative analysis, detection limits for aqueous samples are at the single nanogram level (using relatively simple optical spectrometer systems). The microplasma environment (e.g., kinetic and excitation temperatures) is more in line with combustion flames than other atmospheric pressure plasmas (e.g. ICPs). The robustness of the microplasma with regard to changes in solution matrices is similar to ICP sources. The use of LS-APGD has positive attributes in terms of design simplicity, small footprint, low operating powers, and very low liquid flow rates resulting in no liquid waste. Building on the development of the low power microplasma, the LS-APGD source has brought compactness and low gas and sample consumption to the elemental analysis of flowing samples.

Laser ablation has become a prominent technology for sample introduction in direct chemical analysis of solids, particularly in the case of microanalysis. For analytical purposes, laser ablation has been commonly based on two primary measurement modalities: laser-induced breakdown spectroscopy (LIBS) and laser ablation-inductively coupled plasma-mass spectrometry (LA-ICP-MS). LIBS-based analyses provide unique advantages that include rapid in situ simultaneous multi-element analysis. LA-ICP-MS-based analyses provide enhanced sensitivity and the opportunity of isotopic analysis over LIBS, but require more expensive laboratory-based instrumentation. One of the main advantages of LIBS is in situ analysis—no secondary excitation source. This capability is available because the sampling, vaporization, and excitation processes are complete in one step, while in the case of LA-ICP-MS, the sampling and vaporization/excitation/ionization processes are completed in separate (in time and space) steps; consequently they may be individually optimized.

In both technologies, a focused laser beam converts a small portion of a solid sample into an aerosol. For LA-ICP-MS, the ideal analyte of the aerosol is comprised of small, uniform-sized particles that can be entrained and transported efficiently to the ICP. For LIBS, the ideal analyte of the aerosol is vapor that is excited to atomic and ionic optical emission, as particulates do not contribute to the measurement. Fundamentally, both aerosol forms can be produced, as well as aerosols carrying liquid phase analyte, with the composition established by the experimental (ablation) parameters.

For LIBS, the most successful way (to date) to improve sensitivity has been by increasing excitation efficiency in the laser-induced plasma with the use of a second laser pulse (double pulse, DP) delayed from the sampling pulse. The enhancement in spectral line emission intensity using DP excitation depends on several parameters, including inter-pulse delay time, plasma density, laser wavelength, and line excitation energy. The enhancement is proposed to be due to higher plasma temperature and/or larger and longer plasma duration, as well as increased ablated mass (particularly in the case of collinear configurations). Extension to the use of the ICP source to enhance the analyte excitation/ionization is well characterized and implemented across a diverse range of applications. However, there still exist questions as to the practicality of using a 1-2.5 kW rf plasma, and having a sampling volume of about 1 cm$^3$ to analyze sample mass on the order of nanograms and below.

Overall, laser ablation is well established as an excellent method for direct solid sampling and introduction of the sample into conventional spectroscopic sources such as the ICP. The method allows real-time analysis without sample preparation and requires a significantly lower quantity of mass than conventional sample dissolution procedures. Research over the years has addressed laser wavelength and pulse duration as critical parameters defining accuracy, sensitivity and precision. The femtosecond pulsed ablation process has been shown to produce a narrow, nanometer-sized, particle distribution that is ideal for consumption in the ICP. However, as the spatial resolution is improved and the quantity of sampled mass is significantly reduced, the conventional ICP torch becomes a rather large diluting source that is not necessary for the digestion of femtograms or less material.

What is needed in the art are secondary sources for vaporization, excitation, and/or ionization of an analyte that are of physical dimensions that are complementary to the small sample sizes such as are present in laser ablation samples. It would be highly beneficial if such sources were available at much lower operational costs, smaller footprint, lower energy consumption, and with a practical cost to benefit ratio.

SUMMARY

According to one embodiment, a liquid sampling, atmospheric pressure, glow discharge device is disclosed. For instance, the device can include a first hollow capillary having a discharge end and a counter electrode that is disposed at a distance from the discharge end of the first hollow capillary. The counter electrode is the terminal portion of a second hollow capillary. The device also includes a power source that is in electrical communication with a conductive element in the first hollow capillary and also in communication with the counter electrode. The power source is configured to maintain a glow discharge in a glow discharge space. The glow discharge space comprises a space in which a flow discharged from the first hollow capillary intersects a flow discharged from the second hollow capillary.

A system is also disclosed that includes a liquid sampling, atmospheric pressure, glow discharge device and a laser ablation device. The laser ablation device can be in fluid communication with the glow discharge device such that an aerosol carrying an analyte can flow from the laser ablation device and through the second hollow capillary to be discharged into the glow discharge space of the glow discharge device. During use, the glow discharge space can comprise a microplasma. The system can also include an instrument for analyzing the analyte of the aerosol following interaction of the analyte with the microplasma. The instrument can be, for instance, a monochromator or a mass spectrometer.

In another embodiment a method for examining an analyte is disclosed. The method can include flowing an electrolyte solution through a first hollow capillary of a liquid sampling, atmospheric pressure, glow discharge device such that the electrolyte solution is discharged from a discharge end of the first hollow capillary. The first hollow capillary can include an electrically conductive element that is upstream of or at the discharge end of the first hollow capillary and in electrical communication with the electrolyte solution that flows within the first hollow capillary. The method also includes flowing an aerosol that contains an analyte through a second hollow capillary such that the analyte is discharged from a discharge end of the second hollow capillary. The discharge end of the second hollow capillary being a counter electrode. The method further includes connecting a power source between the electrically conductive element and the counter electrode so as to maintain a glow discharge in a glow discharge space, the glow discharge space comprising a space in which flow discharged from the first hollow capillary and flow discharged from the second hollow capillary intersect. When the aerosol is discharged from the second hollow capillary and into the glow discharge space, the analyte of the aerosol can interact with a microplasma formed within the glow discharge space and move to a higher energy state. For instance, the interaction between the microplasma and the analyte can lead to the analyte being vaporized, excited, and or ionized by the microplasma. Following this interaction, the analyte can be examined as desired.

BRIEF DESCRIPTION OF THE DRAWINGS

The present disclosure may be better understood with reference to the following figures in which:

FIG. 5A and FIG. 5B schematically present from a cross-sectional view, alternative relative orientations of the counter-electrode to the discharge end of the first hollow capillary of an LS-APGD.

FIG. 6 schematically illustrates from a cross-sectional view another orientation of the counter-electrode to the discharge end of the first hollow capillary.

FIG. 9 compares the ion intensities produced by the femtosecond laser ablation of a copper shard, m/z=62.93, and a common hydrocarbon background contaminant $C_4H_7$, m/z=55.06.

FIG. 10 illustrates the depth-profile of a U.S. one cent coin using 110 femtosecond laser pulses at 100 Hz. Cu and Zn onset are nearly simultaneous owing to the high repetition rate of the laser. Background contaminant ion, $C_4H_7$, is also shown.

FIG. 11 illustrates the major isotopes of Pb (FIG. 11A) and Cu (FIG. 11B) generated by the laser ablation of commercial solder and ionized with the LS-APGD ionization source.

FIG. 12 illustrates the expanded mass range spectrum of solder showing its major constituents, Sn and Pb, with associated hydroxide, water and aluminum clusters.

The same reference characters are assigned to the same components throughout the drawings and description.

DETAILED DESCRIPTION

Figure 1:
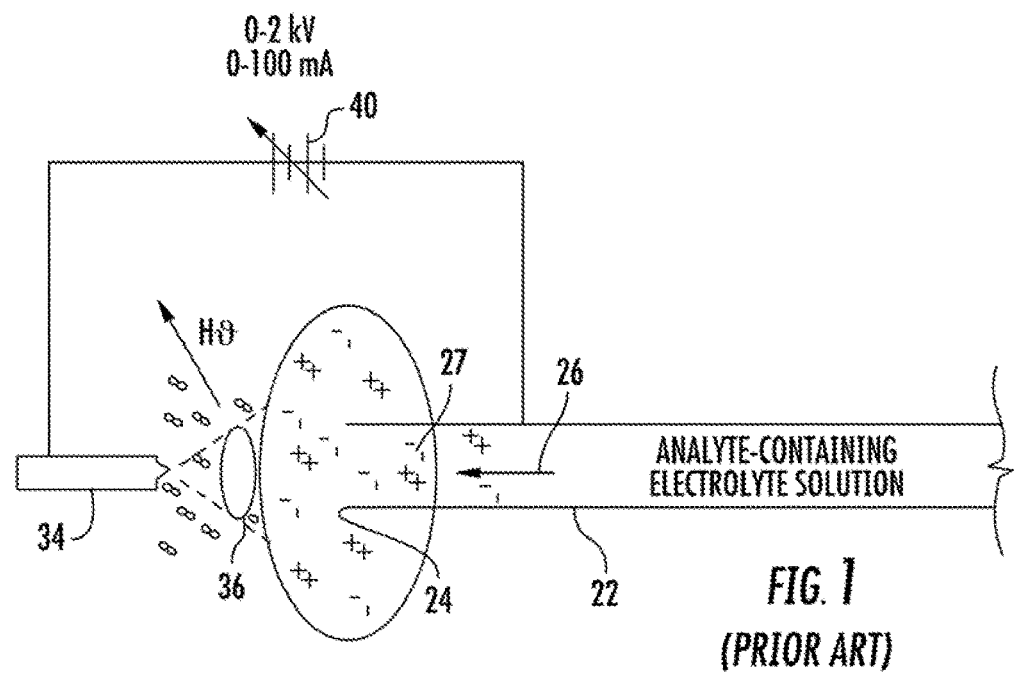
FIG. 1 is a diagrammatic representation of the operation of a prior art embodiment of an LS-APG apparatus.

Reference now will be made in detail to embodiments of the disclosed subject matter, one or more examples of which are illustrated in the accompanying drawings. Each embodiment is provided by way of explanation of the subject matter, not limitation of the subject matter. In fact, it will be apparent to those skilled in the art that various modifications and variations can be made in the present disclosure without departing from the scope or spirit of the subject matter. For instance, features illustrated or described as part of one embodiment can be used on another embodiment to yield a still further embodiment. Thus, it is intended that the present disclosure cover such modifications and variations as come within the scope of the appended claims and their equivalents.

In general, disclosed herein is a liquid sampling, atmospheric pressure, glow discharge (LS-APGD) device as well as systems that incorporate the device and methods for using the device and systems. More specifically, the LS-APGD includes a hollow capillary for delivering an electrolyte solution to a glow discharge space. The device also includes a counter electrode in the form of a second hollow capillary that can deliver an aerosol containing the analyte into the glow discharge space. A voltage across the electrolyte solution and the counter electrode creates the microplasma within the glow discharge space. The analyte of the aerosol can then be acted upon by the microplasma. Depending upon the nature of the analyte, the microplasma can vaporize, excite, and/or ionize the analyte. For instance, an analyte that is in the liquid or solid phase can first be vaporized by the microplasma followed by excitation and optionally also ionization, depending upon the nature of the analyte and the microplasma. An analyte that is already in a gaseous state can be excited and/or ionized by the microplasma.

The disclosed LS-APGD device can be similar to previously known devices, but incorporate the hollow capillary counter electrode. The LS-APGD devices can be particularly useful when analyzing aerosols containing particulate analytes, and in one embodiment, laser ablated particulates. However, it should be understood that the analyte of the aerosol can alternatively be in the gas phase or the liquid phase. In one embodiment, the device can be utilized in conjunction with a laser ablation device, for instance in an analysis system that can also include one or more instruments such as a polychromator, a monochromator, and/or a mass spectrometer for analyzing ions formed in the microplasma.

The disclosed devices can facilitate the direct introduction of the analyte into the microplasma as well as the use of the low power microplasma for exciting/ionizing the analyte. This can be especially beneficial when considering analyte samples of a small volume, such as may be formed in a laser ablation process. Moreover, it has been found that the glow discharge microplasma has sufficient thermal energy and electron number density such that extremely small analyte particles can be analyzed. For example, nano-sized particles on a single nanometer scale (e.g., less than about 10 nanometers) as may be formed from femtosecond pulsed laser ablation process can be ionized by use of the LS-APGD device. In addition, combining a particulate analyte source such as a laser ablation device and the LS-APGD device with an analysis device such as a monochromator and/or a mass spectrometer can be straight forward.

Figure 2:
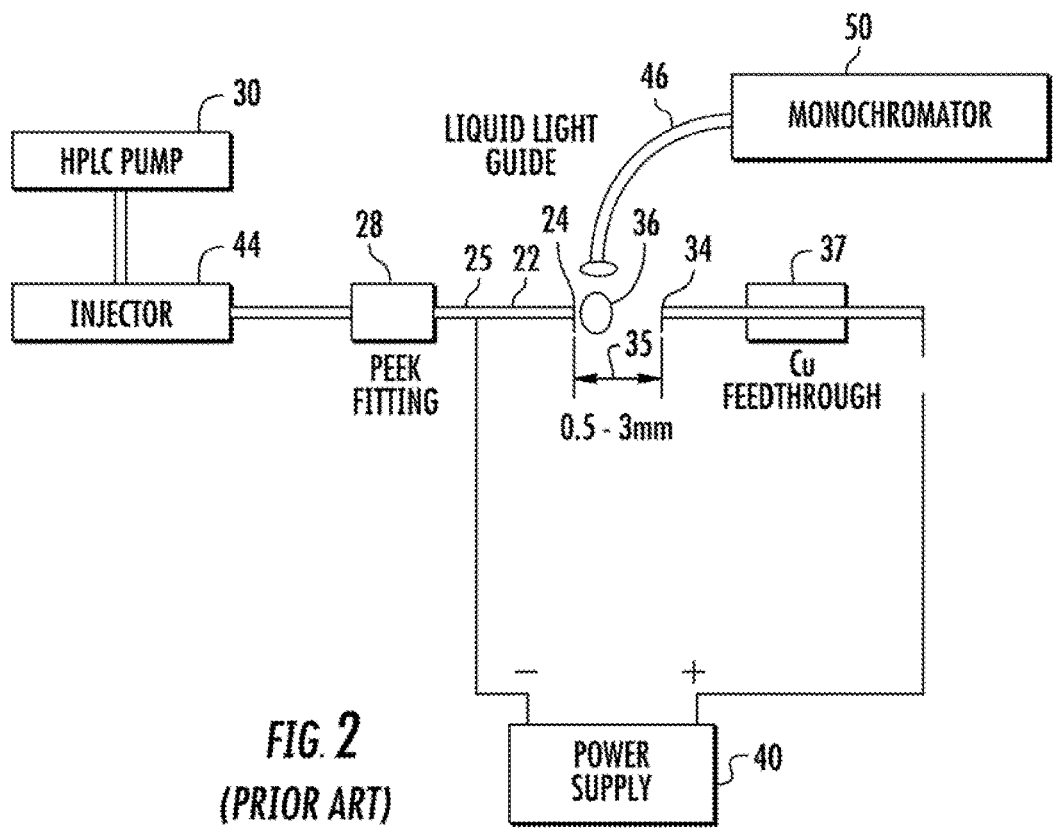
FIG. 2 is a diagrammatic representation of a prior art LS-APGD apparatus operating in an optical emission mode.

FIG. 1 and FIG. 2 generally describe previously known LS-APGD devices. As can be seen with reference to FIG. 1 and FIG. 2, an LS-APGD device can include a power supply 40. The devices also include a capillary 22 through which an electrolyte solution 27 can flow. In these devices, the analyte to be excited/ionized is contained within the electrolyte solution 27. For instance, as shown in FIG. 2, a device can include a pump 30, an injector 44, and a fitting 28 connecting electrically insulative and an electrically conductive portions of the capillary 22 to provide the analyte within the electrolyte solution 27 that passes through the capillary 22 and to the discharge end 24 of the capillary 22. As shown, the capillary 22 defines a longitudinal axis 26 aligned parallel to the direction of the flow of the electrolyte solution 27. The discharge end 24 is a free end that terminates in a plane that is generally perpendicular to the axis 26 of fluid flow upon exiting of the discharge end 24 of the capillary 22.

The devices of FIG. 1 and FIG. 2 include a solid counter-electrode 34 that is axially aligned with the direction 26 of fluid flow upon exiting of the discharge end 24 of the capillary 22. The counter-electrode 34 is disposed at a predetermined distance from the discharge end 24 of the capillary 22 forming a glow discharge space 35 in which the glow discharge 36 containing the microplasma is formed. The power supply 40 is in electrical contact with a conductive element 25 (for instance an electrically conductive capillary section) in the hollow capillary 22 that is in turn in electrical communication with the electrolyte solution 27 within the capillary 22. Thus, the electrolyte solution 27 and the counter-electrode 34 form the input and output electrodes of the LS-APGD apparatus. The analyte species in the higher energy state induced by the microplasma of the glow discharge 36 can be analyzed by use of a suitable analysis device, such as a light directing element 46 in communication with a monochromator 50, as shown.

Figure 3:
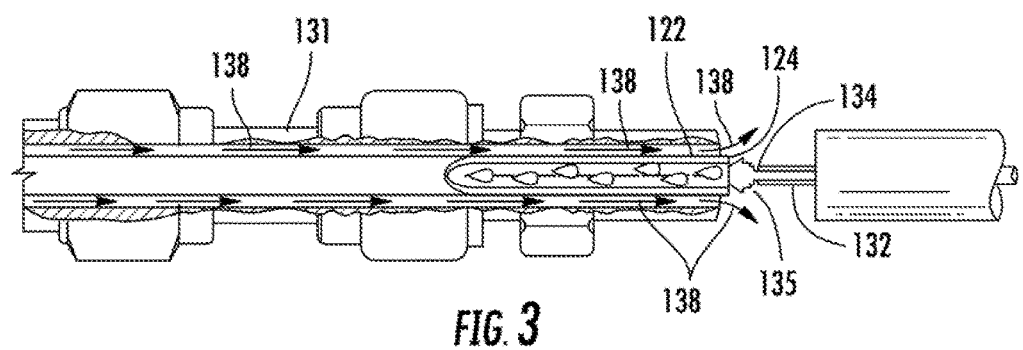
FIG. 3 is a diagrammatic representation of an LS-APGD as described herein.

The disclosed LS-APGD devices differ from previously known devices such as those illustrated in FIG. 1 and FIG. 2 in that an analyte is delivered to the glow discharge space via a second hollow capillary rather than in conjunction with the electrolyte solution. For instance, FIG. 3 illustrates a portion of a device that includes the glow discharge space 135 defined between the discharge end 124 of a first hollow capillary 122 and the discharge end 134 of a second hollow capillary 132. In general, the glow discharge space 135 can be defined within the distance between the discharge end 124 of the first hollow capillary 122 and the discharge end 134 of the second hollow capillary 132. For example, the distance that defines the glow discharge space 135 can be from about 0.1 mm to about 5 mm. More specifically, the glow discharge space 135 can encompass that area in which the flow that is discharged from the first hollow capillary and the flow that is discharged from the second hollow capillary will intersect, thus injecting the analyte carried by the second hollow capillary into the microplasma of the glow discharge.

The size of the glow discharge space can also be variable on a device. For instance, one or both of the discharge ends of the first hollow capillary and the second hollow capillary can be selectively movable so that the size and/or configuration of the glow discharge space 135 can be varied.

At least a portion of the first and second hollow capillaries 122, 132 can be in electrical communication with a power source. The power source is not particularly limited. For instance, the power source can be a direct current source. In other embodiments, the power source can be a radio frequency power source, a microwave frequency power source, or any other suitable power source as is generally known in the art. A suitable direct current power source for maintaining the glow discharge can be provided by a Kepco (Flushing, N.Y.) Model BHA 2000-0.1M power supply.

In one embodiment, the discharge end 124 of the first hollow capillary 122 can be formed of a material that is electrically conductive, such as a metal, e.g., stainless steel. This is not a requirement of the device, however. As the electrolyte solution carried within the first hollow capillary 122 functions as an electrode during use, the discharge end 124 of the first hollow capillary 122 can alternatively be formed of a material that is electrically insulating (such as a polymer (e.g., PEEK) glass or fused silica for example) and/or material that is electrically semiconducting (such as silicon). In an embodiment in which the discharge end 124 of the first hollow capillary 122 is formed of an electrically insulating material, the first hollow capillary 122 can include an electrically conductive element (such as a capillary section, for instance) at a point upstream of the discharge end 124. By way of example, in one embodiment the first hollow capillary 122 can include an electrically conductive element (either at the discharge end 124 or upstream) of stainless steel.

The discharge end 134 of the second hollow capillary 132 can generally be formed of a conductive material, for instance a metal such as stainless steel, copper, etc. to form the counter electrode of the device.

The inside diameter of the first hollow capillary 122 and the second hollow capillary 132 can be of a size to deliver the relatively low volumes of electrolyte solution and analyte utilized in the disclosed methods. For instance, the inside diameters of the first and second capillaries can independently be from about 0.1 mm to about 2 mm, or from about 0.2 mm to about 0.5 mm in some embodiments.

During use, the power supply can be connected between an electrically conductive element of the first hollow capillary 122 and the discharge end 134 of the second hollow capillary 132. An electrically conductive element of the first hollow capillary 122 can also be in electrical contact with the electrolyte solution that flows through the first hollow capillary so as to place a potential difference in the range of from about 200 volts to about 1,000 volts (direct current) across the electrolyte solution as it exits the discharge end 124 of the first hollow capillary 122 and the discharge end 134 of the second hollow capillary 132.

The polarity of the system can generally depend upon the nature of the electrolyte solution and the analyte to be examined. For instance, while the discharge end 134 of the second hollow capillary 132 is typically the powered (or input) electrode, and the electrolyte solution passes through the first hollow capillary 122 that is typically the output electrode, this is not a requirement of the device, and the opposite polarity can be established in other embodiments.

Figure 4:
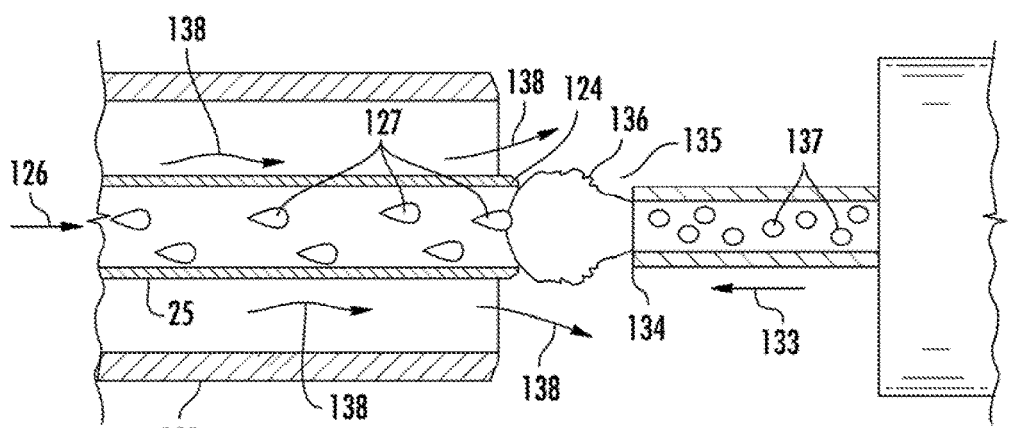
FIG. 4 is an expanded view of a portion taken from FIG. 3.

FIG. 4 is an expanded view of the glow discharge space 135 and surrounding components of an LS-APGD device. As shown, the first hollow capillary 122 can carry an electrolyte solution 127 within the capillary 122 toward the discharge end 124 as indicated by the directional arrow 126. The second hollow capillary 132 can carry an aerosol that carries the analyte 137 within the capillary 132 toward the discharge end 134 as indicated by the directional arrow 133. The LS-APGD generally can include a mechanism for moving the electrolytic solution and the aerosol through the respective capillaries so as to be expelled from the discharge ends of the capillaries. For instance, the electrolytic solution 127 can be expelled from the discharge end 124 of the first hollow capillary 122 at a rate in the range of about 1 microliter per minute ($\mu$/min) to about 5 milliliter per minute (mL/min) at atmospheric pressure. A carrier gas can deliver the analyte as an aerosol to the glow discharge space 135 at a rate in the range of from about 0.1 L/min to about 1 L/min, for instance from about 0.15 L/min to about 0.8 L/min, from about 0.2 L/min to about 0.7 L/min, or from about 0.3 L/min to about 0.6 L/min, in some embodiments.

Flow through the hollow capillaries can be accomplished in a number of ways. For example, a high precision liquid pumping system such as a high performance liquid chromatography (HPLC) pump can be utilized for a liquid flow such as the electrolyte solution through the first hollow capillary 122. The inlet end of the capillary 122 can be connected in fluid communication with the outlet of a pump. One example of such a suitable HPLC pump is a Waters (Milford, Mass.) Model 510 HPLC pump.

In another embodiment, flow through the capillaries can be encouraged by inducing electro-osmotic flow. In this embodiment, a direct current power supply can place an electric potential along the length of a section of one or both of the capillaries 122, 132 that terminates in the discharge end(s) 124, 134. An electric field thus established causes positively charged particles inside the capillary to migrate toward the discharge end. As the positively charged particles move, they carry along the non-charged species due to the effect of the fluid's viscosity, and momentum carries the fluid out of the discharge end of the capillary.

In yet another embodiment, flow through one or both of the capillaries can be accomplished by capillary action.

In one embodiment, the same power supply that is used to move the electrolyte solution through the capillary 122 (e.g., via electro-osmosis) and/or the analyte through the capillary 132 can be used to provide the power needed to maintain the microplasma that is produced at the glow discharge 136 at atmospheric pressure at the glow discharge space 135.

The LS-APGD device can be a glow discharge optical emission spectroscopy (GD-OES) source that operates at atmospheric pressure. As stated, one of the discharge electrodes of the LS-APGD device is the electrolytic solution. The passage of electrical current (either electrons or positive ions) across the solution/gas phase interface causes local heating and the volatilization/excitation/ionization of the analyte species that is discharged into the glow discharge space at the second electrode. As with previously known LS-APGD devices, the LS-APGD can function so as to totally consume an aqueous electrolyte solution at a flow rate of up to about 2 mL/min, i.e., no water drips from the discharge end 124 of the capillary 122. During use, the heat generated by the glow discharge 136 can vaporize the electrolyte solution 127 at the discharge end 124 of the capillary 122.

When an electrolyte solution 127 that has been electrified by the electrically conducting element of the first hollow capillary 122 is consumed as it emerges from the discharge end 124 of the capillary 122, a glow discharge 136 including the microplasma is created between the emerging surface of the exiting electrified electrolyte solution 127 and the discharge end 134 counter electrode of the second hollow capillary 132. The microplasma can have i-V characteristics that are within the range of conventional (abnormal and normal) glow discharges operating in the 0.1 to 10 Torr pressure regime.

In accordance with one embodiment as illustrated in FIG. 3 and FIG. 4, a sheath/cooling gas can flow around at least a portion of the first hollow capillary 122 including the discharge end 124. For example, the terminal portion of the first hollow capillary 122 including the discharge end 124 can be surrounded by a conduit 131 such as a concentric cylinder. This conduit 131 can be connected to a gas supply such as helium, nitrogen or argon gas. The gas flow (indicated schematically by the arrows designated by the numeral 138) around the exterior of the discharge end 124 of the capillary 122 can keep the temperature of the discharge end 124 of the capillary from exceeding the melting temperature of the materials that form the discharge end 124 of the capillary 122. Additionally, the gas 138 exiting from the annular space that is defined between the exterior of the discharge end 124 of the capillary 122 and the interior of the surrounding cylinder 131 is believed to confine the plasma of the glow discharge 136 more tightly around the longitudinal axis 126 of the discharge end 124 of the capillary 122. Furthermore, the gas 138 exiting from the annular space that is defined between the exterior of the discharge end 124 of the capillary 122 and the interior of the surrounding cylinder 131 is believed to create an environment that is especially conducive to the formation of the glow discharge 36 and can help improve the temporal stability of the plasma. When included, the gas flow rate of a surrounding gas flow 138 can generally be from about 0.5 mL/min to about 2 L/min, for instance from about 1 mL/min to about 1 L/min in one embodiment.

While the second hollow capillary 132 is shown aligned at about 180° with the longitudinal axis 126 of the discharge end 124 of the capillary 122 in FIG. 3 and FIG. 4, it should be understood that this alignment is not required and the discharge end 124 of the first hollow capillary 122 and the discharge end 134 of the second hollow capillary 132 can be aligned in any desired configuration where additional room or a different angle is desired. For instance, a particular configuration between the two can be provided to accommodate the inlet of a mass spectrometer.

By way of example, as shown schematically in FIG. 5A, the discharge end 124 of the first hollow capillary 122 can be disposed such that the longitudinal axis 126 of the capillary 122 at the discharge end 124 is disposed in axial alignment with one another, as shown above, and this axial alignment can be in any plane. In one embodiment, an axial alignment of the capillaries 122, 132 can serve to improve containment of the microplasma formed in the glow discharge space 135 and may increase retention time of an analyte within the microplasma.

FIG. 5B illustrates another arrangement between the first hollow capillary 122 and the second hollow capillary 132. As can be seen, in this embodiment the second hollow capillary 132 is not disposed in symmetrical axial alignment with the axis 126 of the first hollow capillary 122. Rather, in this embodiment, the longitudinal axis of the second hollow capillary 132 is disposed at an angle to the axial direction 126 of electrolyte flow from the discharge end 124 of the capillary 122. This angle can be varied depending upon the system parameters. For instance the angle between the longitudinal axis of the first hollow capillary and the longitudinal axis of the second hollow capillary can be less than 90°, about 90°, or greater than 90°.

FIG. 6 illustrates another embodiment of an arrangement between the first hollow capillary 122 and the second hollow capillary 132 of an LS-APGD device. As can be seen, in this embodiment, the first hollow capillary is surrounded by a cylinder 131 through which can flow a gas 138 that can be fed to the annular space of the cylinder. The two hollow capillaries 122, 132 are at a 40° to one another with the glow discharge 136 formed in the glow discharge space 135 where the flow of the electrolyte solution 127 that exits the discharge end 124 of the first hollow capillary 122 and the flow of the analyte 137 that exits the discharge end 134 of the second hollow capillary 132 intersect. The microplasma of the glow discharge 136 can increase the energy of the analyte for evaluation by a suitable instrument 142. A voltage difference can be established by use of a power supply 140 in electrical communication with the second hollow capillary 132 such that the discharge end 134 of the second hollow capillary 132 is a counter electrode and also in electrical communication with a conductive element of the first hollow capillary 122. The electrical circuit can include standard components as desired such as resistors 141 and the like.

In general, the electrically conducting element of the first hollow capillary 122 can be electrically insulated from the rest of the apparatus that is disposed upstream from the electrically conducting element. This can be accomplished for example by providing an electrically insulating conduit that forms the portion of the capillary 122 that is disposed upstream from the electrically conducting element (e.g., a metallic section). In an alternate embodiment, the first hollow capillary 122 can be formed entirely of electrically insulating material (e.g., polyetherether ketone (PEEK)) and the electrically conducting element can be formed as an electrically conducting probe (such as a metal wire) that enters the interior of the capillary 122 through a side wall of the capillary.

The LS-APGD affords the option of applying a voltage across the glow discharge space in any of four ways: (1) the electrolytic solution grounded acting as the anode of the circuit; (2) the electrolytic solution powered as the anode of the circuit; (3) the electrolytic solution grounded as the cathode of the circuit; and (4) the electrolytic solution powered as the cathode of the circuit. The electrode that is at the more negative potential always serves as the cathode. For instance, in one embodiment, the electrically conducting element of the first hollow capillary 122 can be electrically connected to the electrical power supply so as to become the powered (or input) electrode while the discharge end 134 of the second hollow capillary 132 can become the output electrode.

Figure 7:
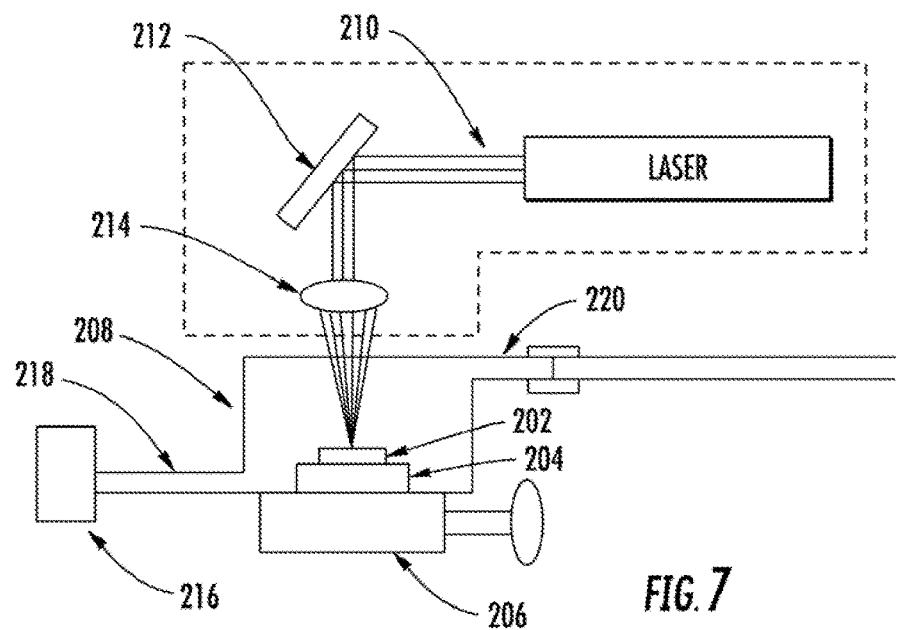
FIG. 7 schematically illustrates one embodiment of a laser ablation device as may be utilized in conjunction with an LS-APGD device as disclosed herein.

According to one embodiment, the LS-APGD device can be utilized in conjunction with a laser ablation device, which can provide the analyte 137 that is carried in the second hollow capillary 134. FIG. 7 schematically illustrates one embodiment of a laser ablation device as may be utilized in such a system. The laser ablation system can direct electromagnetic energy in the form of a laser beam 210 from a laser to a solid sample 202 causing at least a portion of the solid sample 202 to be ablated and forming particles, or in the case of LIBS, causing the solid sample to be vaporized. In one embodiment, the laser can form analyte particles of a size on the single nanogram scale. By way of example, a femtosecond pulsed laser, such as has been utilized in the past in conjunction with inductively coupled plasmas can be utilized (e.g., a J100 Series femtosecond laser, available from Applied Spectra, Fremont, Calif.). There is no particular limitation on the laser of a laser ablation system, provided it delivers suitable energy to ablate the solid sample. For instance, in one embodiment a yttrium aluminum garnet (YAG)-based laser, e.g., a 1064 nm neodymium:YAG (Nd:YAG) laser with a nanosecond pulse temporal width (e.g., about 5 nanosecond pulse) can be utilized with a solid metal sample.

A carrier gas supply 216 can enter the sample chamber 208 via inlet 218 such that the carrier gas passes through the chamber 208 and picks up the analyte to form an aerosol prior to exit via outlet 220. The carrier gas can generally include any as is generally known in the art such as, without limitation, helium, hydrogen, argon, nitrogen, air, etc. The outlet can be the second hollow capillary that discharges into the glow discharge space of the LS-APGD device or may be a different line, but in fluid communication with the second hollow capillary of the LS-APGD. In general, the carrier gas can be carried at a flow rate of about 1 liter per minute or less, for instance from about 1 milliliter per minute (mL/min) to about 500 mL/min, from about 10 mL/min to about 400 mL/min, or from about 50 mL/min to about 350 mL/min, in some embodiments.

Optionally, and as illustrated in the embodiment of FIG. 7, the laser ablation system can include a reflector 212 for directing the laser beam 210 and a lens 214 that can focus the beam 210 and direct the electromagnetic energy of the laser to the sample 202, for instance with a focused target size of from about 10 to about 1 millimeter.

The sample 202 can be held on a stage 204 that in one embodiment can be mobile, for instance by use of a stepper motor 206, which can cause the stage 204 to move as desired in one, two, or three directions, for instance in steps of about 1 millimeter or less.

Figure 8:
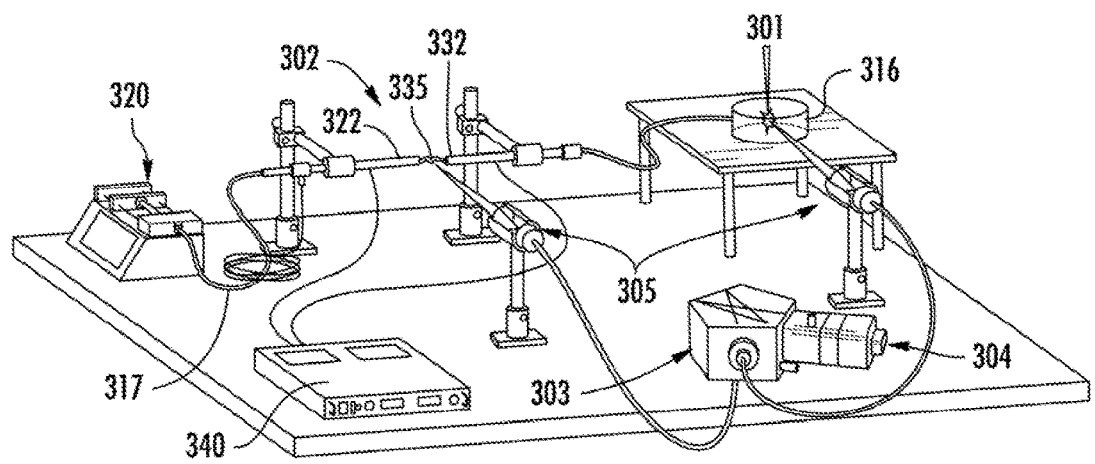
FIG. 8 schematically illustrates one embodiment of an LA-LS-APGD system as described herein operating in an optical emission mode.

The LS-APGD glow discharge device can be provided as a component of a system that can include a laser ablation device and an analysis instrument. For instance, one embodiment of a system is illustrated in FIG. 8. As shown, the system can include a laser ablation device 301, an LS-APGD device 302, and an analysis instrument 303. The LS-APGD device can be a simple and compact source capable of processing an analyte in an aerosol obtained by use of the laser ablation device 301. Analyte of the aerosol generated by laser ablation device 301 can be vaporized, excited, and/or ionized by the LS-APGD device 302 and analyzed by the instrument(s) 303. The laser ablated analyte is transported by means of a carrier gas 316 flowing to the second hollow capillary 332. For instance, the carrier gas can flow at about 1 ml/min through polyurethane tubing connected to the second hollow capillary 332, which is conductive at the discharge end, e.g., a stainless steel capillary. The LS-APGD device produces a microplasma between the electrolyte solution (e.g., a 5% nitric acid solution) delivered by a device 320 such as a syringe pump through the first hollow capillary 322. Optionally, the electrolyte solution can be delivered in conjunction with a sheath gas flow 317 as discussed above. The electrically conductive end of the second hollow capillary 332 functions as the counter electrode, and can be held at about 600 VDC in one embodiment. The first hollow capillary 322 that delivers the electrolyte solution can be, e.g., a fused silica capillary surrounded by an outer stainless steel capillary so as to provide a sheath/cooling gas 317 around the first hollow capillary 322. The sheath/cooling gas flow rate can be about 1 ml/min.

The voltage between the electrolyte solution and the counter electrode can be provided by a power supply 340, and the circuit can include various control devices, e.g., a 10 kilo-ohm, 225 W resistor that can provide ballast between the two electrodes. The geometry of the two hollow capillaries 322, 332 allows the analyte-containing carrier gas aerosol to be injected directly into the plasma for interaction and energy transfer from the plasma to the analyte. The system can include an analysis device such as a spectrograph coupled to an intensified charge-coupled device 304 and can include collection optics 305 directed at the glow discharge space 335 and optionally also at the laser ablation device to affect simultaneous LIBS measurements.

In one embodiment, the electrolyte flow can contain a reference material, for instance a known amount of the analyte or another material that can function as an internal standard during use of the device/system.

Beneficially, it has been found that the microplasma formed by the LS-APGD device can possess sufficient thermal energy to vaporize widely employed nanosecond, infrared laser-produced particles, which are generally larger than those formed via femtosecond ablation. Beyond vaporization, it has also been found that electron collisions in the glow discharge space can be energetic enough to result in optical emission and/or ionization that can then be used for the quantitative determination of analytes in the microplasma volume. The LS-APGD source also offers the possibility of shortening the distance between the sampling chamber and the LS-APGD source, which can increase transport efficiency, as well as independent optimization of the sampling and the vaporization/excitation/ionization processes.

One or more instruments can be used to analyze the excited state species of the glow discharge. By way of example, in one embodiment, a light directing element can be disposed to direct the electromagnetic radiation from the glow discharge that forms in the glow discharge space to a suitable analyzing instrument. A suitable light directing element can include a fiber optic light guide. In one embodiment, one end of a 3 mm core diameter liquid light guide (available from Edmund Industrial Optics, Barington, N.J.) can be disposed so as to sample optical emission from the plasma of the glow discharge formed in the glow discharge space. The opposite end of the light guide can be coupled to an instrument for analyzing electromagnetic radiation that emanates from the glow discharge. A suitable such analyzing instrument can include a monochromator or a polychromator. Specifically, an end of the light guide can be coupled to the entrance slit of an optical spectrometer such as a Digikrom Model 240 monochromator (CVI Laser Corp., Albuquerque, N. Mex.) 0.24 m Czerny-Turner spectrometer equipped with a 2400 groove/mm holographic grating for optical analysis and monitoring of the emission from the sample. The control interface of the monochromator can be used to adjust the scanning range, slit width, spectral calibration, and wavelength selection of the monochromator, as is known.

An analysis instrument can be used in conjunction with other instruments, as is generally known in the art. For instance, a photo-multiplier tube (e.g., from Hamamatsu, Bridgewater, N.J. Model) can be disposed to detect the optical emission signals in the glow discharge. An analog current meter can be connected to the photo-multiplier tube and can convert the optical emission signals into voltage signals. A computer can be employed to record the output of the current meter e.g., via a National Instruments (Austin, Tex.) NB-MIO-16× interface board. An X-Y recorder-type program within the National Instruments LabView 2 software environment can be used to record the data. The obtained digital data can be processed and managed as desired.

A mass spectrometer is another instrument that can be used to analyze constituents of the glow discharge. A commercial inductively-coupled plasma mass spectrometer such as a Model ELAN 6100 instrument available from Perkin-Elmer/Sciex, Ontario, Canada, can be disposed near the plasma of the glow discharge in a conventional manner for analyzing ions that emanate from the glow discharge. In another embodiment, a Thermo Scientific Exactive™ orbitrap mass spectrometer can be utilized.

In one possible implementation, analyte species are ionized through collision with electrons or excited state atoms or through charge exchange with other ionic species, with the products sampled via the ion optics that extracts the ionic species from the plasma of the glow discharge and directs them to a quadrupole mass analyzer. The masses of the molecules and atoms constituting the analyte flow are analyzed by a mass spectrometer such as a quadrupole mass filter (or another type of mass analyzer) that is configured to allow ions with a given mass/charge ratio to reach a detector. As is conventional, a turbo molecular pump can be employed to maintain the mass spectrometer under reduced pressure.

The disclosed LS-APGD can be beneficially utilized for characterization of materials, including aerosols containing micro- and nano-particles using direct solid sampling, for instance via laser ablation. The devices are small, easily built, and easily adaptable as an energy source for analysis methods such as elemental and isotopic mass spectrometry. The LS-APGD has very specific advantages over existing methods which use high power, large volume plasma. Current plasma-based sources rely on powers of up to 2 kW and support gases of up to 16 liters per minute. The present approach involves a much smaller footprint, lower power and gas flow. The size is also more compatible with efficient particle introduction.

The LS-APGD ionization source has been shown previously to be a low cost, compact, and efficient alternative to ICP for the ionization of analytes carried in an electrolytic solution. The analyte delivery method of the disclosed devices can offer further improvements to the analysis systems. Simplicity in design, low liquid and gas consumption, and no liquid waste are all positive attributes that can characterize this method of sample processing for elemental analysis. The presently disclosed devices are capable of processing solid sample particles on the order of about 100 nm or smaller, e.g., generated by laser ablation and delivered by carrier gas as an aerosol.

The present disclosure may be better understood with reference to the examples provided below.

Example 1

Aerosol from bulk solid was generated using an Applied Spectra (Fremont, Calif.) model J100 series femtosecond laser ablation system. The ytterbium-doped laser crystal is directly pumped by laser diodes and, after frequency tripling, delivers 343 nm wavelength light at a spot size of about 80 µm. Each laser pulse is 300-400 femtoseconds in duration with about 110 µJ of energy. The laser repetition rate can be adjusted from 1 Hz to 10 kHz. Results obtained were acquired at 100 Hz. Lead and copper aerosols were generated while moving the sample stage at 10 µm/s, while the depth-profile of a one-cent coin required a stationary sample stage. Sample particles were transported by means of argon gas flowing at 1 L min$^{-1}$ from a 400 cm$^3$ ablation chamber to the ion source through 25 m of polyurethane tubing having a 6 mm o.d. and 4 mm i.d. This length of tubing was necessary to transport the laser ablation aerosol from the laser to the mass spectrometer.

Introduction of the aerosol into the plasma of the LS-APGD utilized a hollow counter-electrode (1.6 mm o.d., 1.0 mm i.d.) connected to the carrier gas tubing with a series of stepped down Swagelok (Solon, Ohio) connections. In addition, the geometry of the electrodes relative to each other and relative to the sampling capillary of the mass spectrometer was altered from previous devices due to the change in the aerodynamic flow brought about by the carrier gas introduction. The configuration used can be seen in FIG. 6.

The cathode consisted of a fused silica capillary (125 µm o.d., 75 µm i.d.) that delivered the electrolyte solution (5% HNO$_3$) required to sustain the plasma, via syringe pump (Fusion 100T, Chemyx, Stafford Tex.) at a flow rate of 10 µl min$^{-1}$, surrounded by a stainless steel capillary (700 µm o.d., 500 µm i.d.) through which flowed Ar sheath/cooling gas at a rate of ~1 L min$^{-1}$. The plasma was generated between the grounded solution (cathode) and a counter electrode (anode) with a constant discharge current of 18 mA. Power to the counter electrode was provided by a Glassman (High Bridge, N.J.) model EH, 100 mA, 1000V power supply through a 10 kΩ, 225 W ballast resistor. The addition of the argon carrier gas brought about significantly more plasma instability that was remedied to some extent by increasing the electrolyte flow and discharge current, however the plasma instability remained an issue and will likely require additional work before full optimization is realized. The distance from the electrodes to the capillary inlet of the mass spectrometer was about 0.5 cm, with the gap between the respective electrodes maintained at a distance of about 1 mm.

Mass analysis was handled by a Thermo Scientific Exactive™ Orbitrap Mass Spectrometer in the positive ion mode. This instrument was designed for an electrospray ionization (ESI) source, and as such, was easily adapted for use with the LS-APGD ionization source, requiring only the removal of the ESI housing. The mass spectrometer was operated using in-source collision induced dissociation (CID) at an energy of 52 eV. This is a value similar to what is used with the ESI source and was utilized in these experiments because it generally produced higher ion intensities in the mass region of interest and lower intensity water clusters. Data analysis was performed with Thermo Scientific XCalibur 2.1 software.

The first sample was a square of oxygen-free hard copper from a UHV conflat flange gasket. The second was a disc of lead (Pb) solder formed by melting several drops from a wire spool onto a flat, cool surface. The last sample was a one-cent U.S. coin. No further preparation was performed for any of the samples.

In order to clearly discern the response of the mass spectrometer to the sample ions relative to the background signal generated by the carrier gas, data acquisition was started before or at the same time as the laser ablation. The plasma as well as the carrier gas was in continuous operation. The 25 m of tubing delivering the ablated particles to the LS-APGD ionization source resulted in a delay time of about 20 seconds between the laser firing and mass spectrometer response. FIG. 9 shows the smoothed (15-pt. boxcar) ion chromatograms of Cu and C$_4$H$_7$ for the femtosecond laser ablation of the Cu target at a repetition rate of 100 Hz and a laser raster speed of 10 µm s$^{-1}$. The C$_4$H$_7$ ion at mass 55.055 amu is one of several common hydrocarbon contaminants in mass spectrometry. It serves, in these experiments, as the baseline mass spectrometer response to the LS-APGD/laser ablation system. In addition to the $C_4H_7$ ion, many other common hydrocarbon ions such as the tropyllium ion (m/z 95) and fragments associated with polydimethylsiloxane (PDMS) were found at m/z 73, 147, 207, 209. The LS-APGD was operated at a discharge current of 18 mA, and an electrolyte flow rate of 10 μl min$^{-1}$.

The laser was activated and deactivated at approximately 30 seconds and at 2 minutes 45 seconds respectively. The instrument response delay was primarily a function of the particle transport tubing. Twenty-five meters of tubing with a 4 mm inner diameter has a volume of ~0.3 L. With a carrier gas flow rate of 1 L min$^{-1}$, the calculated transport time is about 20 s, which corresponds with experimental results. The baseline Cu signal is non-zero both before and after the experiment, with the post analysis intensity slightly elevated relative to the pre-experiment value. The substantial Cu background intensity is likely due to a memory effect caused by previous experiments which resulted in residual Cu particles on the surface of the capillary counter-electrode and/or the mass spectrometer capillary interface. After laser deactivation, washout time was dependent not only on transport tubing length, but also on laser ablation chamber volume. The sample particles that had been ablated were distributed throughout the volume and required time to enter the transport tubing resulting in washout times that exceed response times at the initiation of the experiment. Nevertheless, the response of the mass spectrometer when coupled to the LS-APGD and laser ablation particle source clearly demonstrated the efficacy of the combination of these analytical components for elemental analysis.

To test the plausibility of using an LS-APGD ionization source for a laser ablation depth profiling experiment, a 1994 one-cent U.S. coin was analyzed. Beginning in 1982, a one-cent U.S. coin consists of a 10 μm thick pure Cu shell surrounding a Zn core. While 10 μm is far from the lower limit of depth-resolution capability of laser ablation, it is still a useful experiment in determining if the LS-APGD source can provide adequate ionization efficiency for particles generated at laser powers sufficiently low to resolve the Cu cladding from the Zn core. FIG. 10 shows the results of the laser ablation depth profile of the coin using 110 μJ pulses at a frequency of 100 Hz. The LS-APGD ionization source characteristics were identical to the pure Cu shard experiment.

As in the copper shard experiment, the carrier gas and source plasma were in continuous operation throughout the experiment, while the laser was activated approximately 40 seconds after the start of data acquisition. A minor isotope of Zn was plotted because the intensity more closely matched that of copper, demonstrating the marginally earlier arrival of the Cu particles. The background contaminant ion, $C_4H_7$, is also plotted. Prior to laser activation, both the Cu and hydrocarbon background intensities are significant, and follow a similar trend, while the Zn intensity is zero. As seen with the copper shard experiment, the intensity of the Cu ion prior to laser activation indicates a significant contamination from prior extensive experiments with pure Cu, most likely in the form of particle accumulation on the electrodes and/or sampling orifice. Cu and Zn signal onset occur almost simultaneously at approximately 1 min., owing to the relatively high laser repetition rate and thin Cu cladding. The removal rate of copper is about 200 nm pulse$^{-1}$ which, at the 100 Hz repetition rate used, translates into complete penetration of the Cu cladding in about 0.5 s. Aerosol diffusion over the extended transport tubing results in the extended Cu intensity before the signal drops to near pre-experiment levels after about 30 seconds, though plasma instability results in significant fluctuations of all ion intensities throughout the experiment. Attenuation of ion intensity is common in depth profiling experiments as the aspect ratio (depth/diameter) increases because particles have a more difficult time escaping the crater. This effect can be seen clearly starting within 20 seconds of Zn reaching its peak intensity. Though the trend seems to also appear in the Cu signal, it is much more likely that this results from depletion of Cu particles, rather than crater affects given the thin nature of the cladding relative to the laser spot size (about 80 μm).

The results presented in FIG. 11 were acquired from a disc of rosin-core solder formed by allowing drops of melted solder wire to fall onto a flat surface. The composition of the solder was 60% Sn, 40% Pb and unspecific trace quantities of several other elements including Cu. The laser and LS-APGD conditions were identical to those used for the Cu shard analysis. The three major isotopes of Pb are shown (FIG. 11A), all with mass resolution exceeding 90,000, corresponding to a full width at half maximum value of <3 mDa for the $Pb^{208}$ isotope. Given the inverse relationship between ion mass and resolving power for the orbitrap, the Pb isotope peaks exhibited somewhat lower values than the Cu isotopes, which were acquired with M/ΔM>160,000 (FIG. 11B).

Given the open nature of the LS-APGD ionization source, it is expected that the oxygenated species of the analyte ions will form in significant quantities due to the aqueous nature of the electrolyte solution and possibly the atmospheric gas entrainment around the source and at the entrance to the mass spectrometer. Atomic ions that do form at the source must travel at least several inches, after entering the capillary inlet of the mass spectrometer, through an environment with a short mean-free path before reaching conditions more amenable for reactive metal ions. The expanded mass range spectrum of the commercial solder, illustrated in FIG. 12, shows this effect clearly with extensive oxidation products of the two main constituents, Pb and Sn.

In addition to the common hydroxide and water products, it appeared that aluminum contamination products were also formed. The source of the contamination appeared to originate from the solder, despite the fact that it is not listed as a trace metal component of the solder. None of the source components were known to contain aluminum. Experiments using solder wire as the cathode in conjunction with a solid stainless steel counter-electrode (i.e. no carrier gas or laser ablation particles) produced similar spectra indicating that the source of aluminum did not originate from the laser ablation or carrier gas delivery components.

The spectrum in FIG. 12 is somewhat reminiscent of the adducted elemental spectra of ESI MS. Just as there was not sufficient energy in collisions with the counter-current gas in ESI to remove all matrix adducts (e.g. MeOH, $H_2O$, OH, etc.) it appeared that there was not sufficient energy in the discharge or subsequent collisions to remove all adducts in this case. However, the LS-APGD spectra are less complex than ESI spectra since there is no organic solvent present in the solution to lower the aqueous surface tension as required in ESI. These spectra are also somewhat reminiscent of the early ICP ion trap MS spectra in which case reactions with adventitious water in the three dimensional traps created similar adducts. In the ion trap case the water/oxygen adduct ions were significantly reduced if not eliminated by cryotrapping adventitious water in the ion trap helium atmosphere.

Example 2

An experimental system is depicted in FIG. 8 was utilized. Laser ablation was performed inside a sample chamber of cylindrical shape (7 cm diameter and 3 cm height) with one gas port inlet and one outlet. Helium was used as the carrier gas. The chamber was located about 1 m from the LS-APGD.

The counter-electrode was a nickel, 0.3 cm o.d., 0.1 cm i.d. hollow capillary, the solution electrode (nickel, 0.16 cm o.d., 0.06 cm i.d.) housed an internal fused silica capillary (360 μm o.d., 100 μm i.d. Idex Health and Science). Helium was introduced as the sheath/cooling gas (0.1-0.7 L min$^{-1}$) in between the concentric capillaries with a liquid flow (1-100 μL min$^{-1}$) of 5% HNO$_3$ being introduced through the fused silica capillary using a programmable syringe pump (New Era Pump Systems Inc., model NE-1000 Multi-Phaser). The distance between the two electrodes was kept between about 1 and 2 mm. Power was provided to the counter electrode by a Bertan Model 915 series power supply (0-100 mA, 0-1 kV, Hicksville, N.Y.) that was operated in negative polarity and constant current mode with a 10 kΩ, 225 W ballast resistor.

The laser ablation device utilized a Nd:YAG laser with a 5-ns pulse duration operating at its fundamental wavelength of 1064 nm, at a repetition rate of 5 Hz. The laser beam was focused onto the target perpendicular to the sample surface using a lens with a focal length of 100 mm. The laser energy used for ablation was 44 mJ. The sample was placed on an x, y, z manual stage. After selecting the laser energy based on the APGD signal, LIBS emission signal, and signal-to-background ratios from Cu (324.75 and 515.33 nm) were used to set detector gate delay, width and gain. The operation parameters were:

Laser type and wavelength: Nd:YAG 1064 nm
Pulse duration: 5 ns
Pulse energy: 44 mJ
Repetition rate: 10 Hz
Focal length of the lens: 100 mm
Spot diameter: about 100 μm
Delay time: 1 μs
Gate width: 5 μs
Gain: 1

An intensified charged-coupled device (ICCD) from Princeton Instruments detected optical emissions from both plasmas (LIBS plasma and LS-APGD plasma). The ICCD was triggered from the Q-switch sync output of the laser. An Acton SP2150i spectrograph with a 1200 grooves mm$^{-1}$ grating was used to disperse the atomic emission. The wavelength range of the spectrometer was centered at 320 nm and 515 nm. A fused silica biconvex lens (35 mm focal length, 25.4 mm diameter) was used to focus the emission onto the entrance of an optic fiber, and into the 750 μm entrance slit of the spectrograph. The same detector was used to measure emission from the LS-APGD; in this case the spectrometer was used in shutter mode because the microplasma was continuous.

A pure copper standard (Goodfellow, Oakdale, Pa., USA) was used to evaluate the LS-APGD performance. A set of copper-zinc binary alloys (Glen Spectra reference materials (Middlesex, UK) was used to assess the quantitative aspects of the LS-APGD as a potential second excitation source for laser ablation. The alloy compositions are provided in the table, below.

| CRM | Zn (%) | Cu (%) | Zn/Cu |
|---|---|---|---|
| 1 | 48.5 | 51.5 | 0.943 |
| 2 | 44.4 | 55.5 | 0.799 |
| 5 | 30.5 | 69.5 | 0.439 |
| 7 | 17.5 | 82.5 | 0.212 |
| 9 | 10.5 | 89.5 | 0.117 |
| 10 | 6.2 | 93.8 | 0.066 |

The sample surfaces were slightly polished and then cleaned with ethanol prior to the ablation to improve the reproducibility of the measurements. Two hundred (200) laser shots at 5 Hz were delivered to each position on the sample, with the measured optical intensities integrated over the duration of the experiment. Measurements from three different locations of each of the samples were performed and the mean and standard deviation of these three measurements were used for the plots.

The mean particle size in this application could reach up to 2 μm. The configuration utilizes a 180° geometry (collinear with respect to the solution electrode and counter electrode), which was found to be an optimal geometry for optical emission studies. In the case of LA sampling, this geometry also ensured the longest residence time in the plasma. Systematic parameter evaluations were conducted. The parameters of interest included: particle carrier gas flow rate (helium), glow discharge current, laser energy, and the solution electrode sheath gas and liquid flow rates. The quantitative performance was assessed using the brass alloy reference materials, with comparison of results to LA-ICP-OES.

Figure 13:
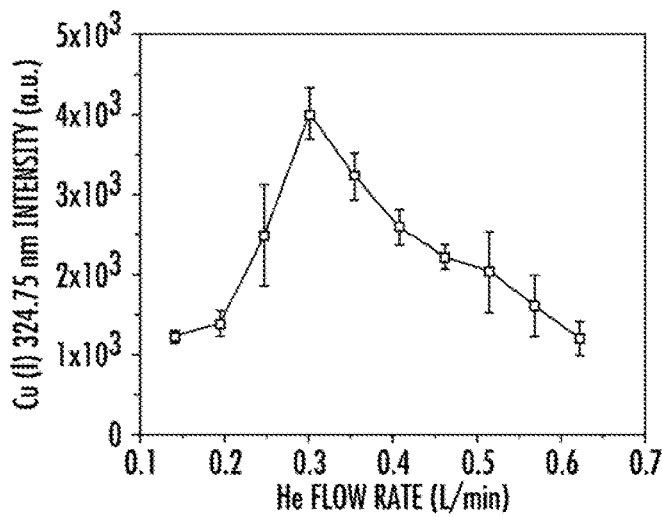
FIG. 13 illustrates the influence of the helium carrier gas flow rate (0.14-0.63 L min−1) on ablated Cu (I) response from an LS-APGD microplasma. Background response≈$1.2×10^3$. All other parameters constant: discharge current=60 mA, solution flow rate=10 μL min$^{-1}$ (5% $HNO_3$), sheath gas=0.3 L min$^{-1}$ He, 1064 nm laser=55 mJ (rep rate=5 Hz).

The OES response of the ablated material to changes to the microplasma sheath gas flow rate, the flow rate of the electrolytic solution (5% HNO$_3$), and the carrier gas (transporting the ablated particles into the plasma) flow rates are interrelated. The LS-APGD was initially optimized using a copper standard solution to ensure proper operation prior to introducing ablated particles. FIG. 13 shows the Cu (I) 324.75 nm response for ablated particles introduced into the plasma via the helium carrier gas, operated from 0.15 to 0.62 L min$^{-1}$. The maximum copper response was found using a helium carrier gas flow of 0.30 L min$^{-1}$. At flow rates <0.3 L min$^{-1}$, a large drop in intensity was measured, likely due to poor transport from the sample chamber to the LS-APGD. At flow rates ≥0.35 L min$^{-1}$, the drop in intensity was more gradual than at low flow rates, suggesting that particles were reaching the LS-APGD, but passing through the plasma faster than they could be vaporized/excited. The velocity of the carrier gas under the optimum 0.3 L min$^{-1}$ flow rate suggests a plasma residence time of about 1 ms.

The electrolyte solution (5% HNO$_3$) through the glass capillary was delivered at rates of 1-100 μL min$^{-1}$ while measuring the emission of the ablated copper particles introduced by the carrier gas flow rate of 0.30 L min$^{-1}$. In this implementation of the LS-APGD, the solution flow rate controlled the delivery of current carrying charge to the surface of the liquid electrode as well as the solvent loading into the plasma.

Measurements revealed that at flow rates of 1-25 μL min$^{-1}$ the copper response was consistent, but as the flow rate was increased from 25 to 100 μL min$^{-1}$ the intensity began to drop and the precision was compromised. At this discharge current (60 mA), the higher solution flow rates consumed more of the total plasma energy and affect the solution evaporation and gas phase excitation processes.

The sheath gas flow surrounding the liquid capillary of the microplasma served to provide stability, particularly at low liquid flow rates. Using a flow rate of 10 μL min$^{-1}$ (5% HNO$_3$) and a particle carrier gas flow of 0.30 L min$^{-1}$, the flow rate of the sheath helium gas was varied from 0.13 to 0.57 L min$^{-1}$. The maximum copper response was measured using flow rates between 0.13 and 0.23 L min$^{-1}$, with a gradual drop in copper intensity found at flow rates ≥0.27 L min$^{-1}$. As the sheath gas was increased above 0.3 L min$^{-1}$ the path of the particles were likely impeded due to turbulence in the counter flow of helium gas. An attempt to operate the LS-APGD source with no sheath gas resulted in overheating and melting of the capillary and solution electrode tip. The optimized conditions of 0.30 L min$^{-1}$ helium carrier gas flow, 0.20 L min$^{-1}$ helium sheath gas flow, and a liquid flow rate of 10 μL min$^{-1}$ 5% HNO$_3$ were employed throughout the remainder of these studies.

Figure 14:
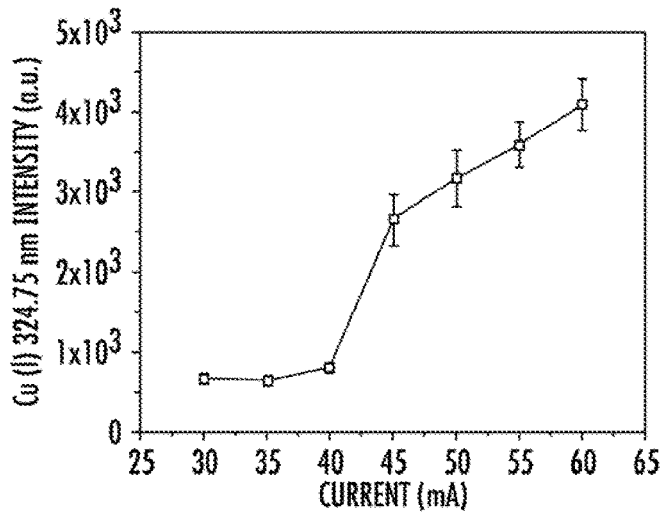
FIG. 14 illustrates the Cu (I) emission response as a function of the APGD source current. Background response≈$0.6×10^3$. All other parameters constant: particle carrier gas=0.3 L min$^{-1}$, solution flow rate=10 μL min$^{-1}$ (5% $HNO_3$), sheath gas=0.3 L min$^{-1}$ He, 1064 nm laser=55 mJ (rep rate=5 Hz).

The analyte excitation was found to be most efficient at relatively higher currents (≥35 mA). FIG. 14 displays the Cu (I) response as a function of glow discharge current for particles introduced from ablation of the copper target. It takes ≥45 mA of current to excite the ablated copper particles, with essentially no signal detected below 45 mA. The particles ablated from the 1064 nm nanosecond pulsed laser were relatively large, and thus it is reasonable to suggest that more energy was required to vaporize and excite them as compared to experiments where the plasma was operated at a current of 10 mA. The remainder of the experiment was carried out using a glow discharge current of 60 mA.

Figure 15:
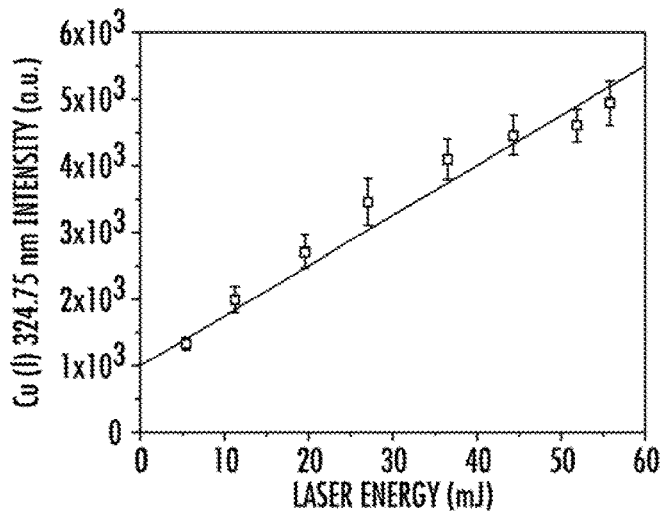
FIG. 15 illustrates Cu (I) emission response as a function of laser power. Background response≈$1.2×10^3$. All other parameters constant: discharge current=60 mA, particle carrier gas=0.3 L min$^{-1}$, solution flow rate=10 μL min$^{-1}$ (5% $HNO_3$), sheath gas=0.3 L min$^{-1}$ He, 1064 nm laser rep rate=5 Hz.

The final operational parameter studied was the incident laser energy. The incident laser energy affects two processes; the size of the ablated particles and the total ablated mass per unit time. FIG. 15 shows a linear fit to the Cu (I) intensity as a function of laser energy. While the response looks to be fairly proportional to the input power, there is some indication that there may be an onset of saturation of the process. Overall, it is believed that the plasma was not overloaded with ablated particles in these experiments. A laser energy of 44 mJ was chosen for the remainder of the example.

Figure 16A:
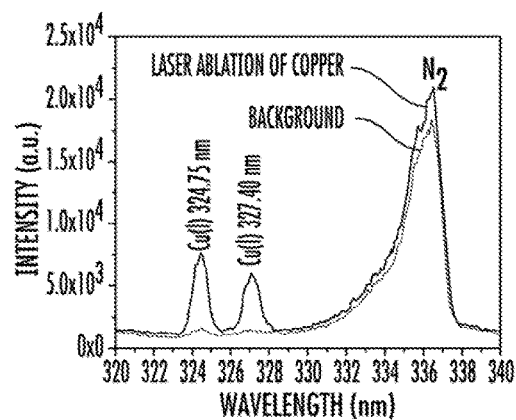
FIG. 16 illustrates the laser ablated LS-APGD optical emission spectra measured from a copper sample from 320 nm to 340 nm (FIG. 16A) and from 506 nm to 526 nm (FIG. 16B). Experimental conditions: discharge current=60 mA, particle carrier gas=0.3 L min$^{-1}$, solution flow rate=10 μL min$^{-1}$ (5% $HNO_3$), sheath gas=0.3 L min$^{-1}$ He, 1064 nm laser=44.3 mJ (rep rate=5 Hz).
Figure 16B:
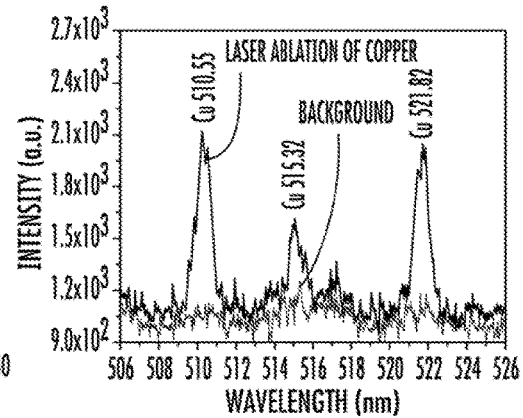

FIG. 16 represents a typical optical emission spectrum collected from a copper standard ablated into the LS-APGD using the optimized conditions. The copper emission at wavelengths of 324.75, 327.39, 510.55, 515.33, and 521.82 nm is clearly discernible from the background obtained when particles are not ablated into the LS-APGD source. The large band, with a maximum at 337.13 nm corresponds to emission of the molecular band N$_2$C$_3$Π-B$_3$Π (0,0), most likely from the nitrogen in air and/or perhaps the nitric acid solution used to sustain the plasma.

Figure 17:
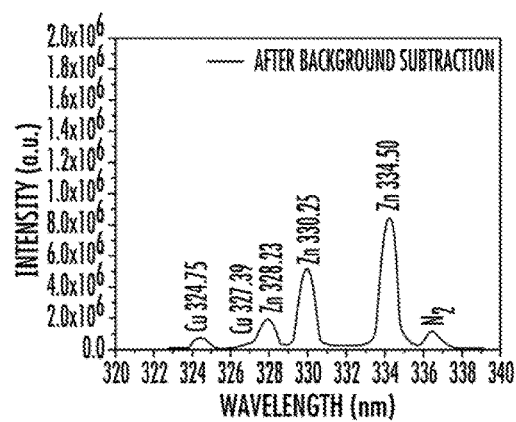
FIG. 17 illustrates the laser ablated LS-APGD optical emission spectrum measured from a brass alloy. Working parameters same as listed in FIG. 16.

The set of alloys was ablated and analyzed by both LA-LS-APGD and LIBS. These alloys have been studied extensively using LA-ICP-MS in this laboratory, providing a benchmark for understanding the laser ablated LS-APGD and LIBS measurements. Analysis by LIBS provided a non-linearity calibration response, with a good response to Zn-containing smaller particles, and poor sensitivity to larger Cu particles. When Cu was used as an internal standard, a linear calibration response was measured for the Zn/Cu alloy standards. FIG. 17 is illustrative of the spectra measured from the LS-APGD in the ablation of brass alloys, in this case alloy #1 (51.5% Cu/48.5% Zn). The spectra derived from the LS-APGD excitation source are similar in composition (relative to the species' contributions) to direct LIBS analysis of brass samples. The spectra reflect nucleation and condensation from the vapor, producing smaller particles which are Zn-rich due to its much lower vaporization temperature in comparison to Cu. Copper is more difficult to vaporize and instead larger copper particles are ejected from the melted surface of the brass alloy and transported into the plasma region. The separate role of fractionation during laser ablation versus that which may occur in the LS-APGD has not been addressed.

Figure 18:
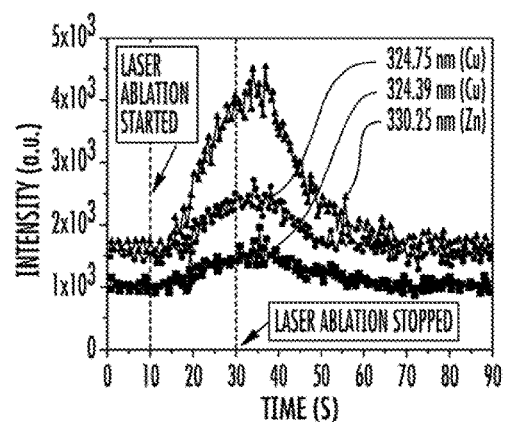
FIG. 18 illustrates laser ablated LS-APGD optical emission signal transients of Cu (I) (324.75 and 327.39 nm) and Zn (I) (330.25 nm) for particles ablated from a brass alloy. Working parameters same as listed in FIG. 16.

With low repetition rate sample introduction, there is a temporal component to the measured response, reflective of the particulate transport to the excitation/ionization source. FIG. 18 shows the transient response for two Cu (I) emission lines and one corresponding to Zn (I) for the laser ablated LS-APGD microplasma. These data show how intensities increase during the time the laser is on, reaching maximum values at the same time, with a slow decrease when the laser is switched off. Particles were found to take about 3.5 seconds to reach the LS-APGD source from the sampling chamber. The fact that these two elemental species were well correlated suggests that either the plasma was efficient at vaporizing the various particle sizes or that only the smaller fraction of particles was transported.

Figure 19:
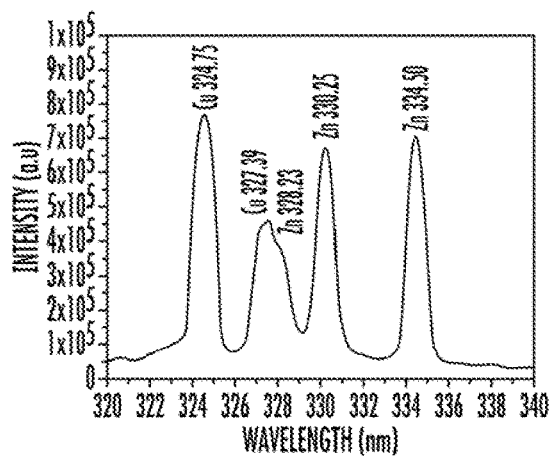
FIG. 19 illustrates the LIBS optical emission spectra measured for a brass alloy.

While the optical spectra of the LA particles in the microplasma can be treated as a transient on a continuous background, the LIBS spectra must be time-gated from background plasma continua on a single-pulse basis. FIG. 19 shows a typical spectrum obtained from direct observation of the LIBS emission for the same brass alloy as FIG. 17 using the procedure parameters of Table 1. All relevant emission lines in this region for Cu and Zn are observed and, in contrast to the spectra obtained from laser ablated LS-APGD emission, no N$_2$ band was observed (e.g., FIG. 16A). In comparison of FIG. 19 and FIG. 17, differences in the excitation conditions between the LS-APGD and LIBS plasmas as the higher-lying Zn (I) lines are more prevalent than the Cu (I) resonant transitions. In general, the S/B for the Zn (I) lines from the microplasma are ~2× those of the LIBS source, with Cu (I) being quite comparable.

Figure 20:
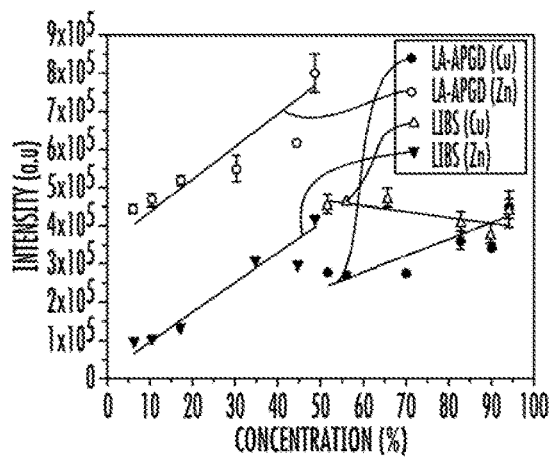
FIG. 20 illustrates the Cu (I) 324.75 nm and Zn (I) 330.25 nm responses with respect to the known percentage of each element across a brass standard alloy series using LS-APGD and LIBS optical emission spectrometry.

The quantitative characteristics of the laser ablated LS-APGD and LIBS methods were compared using the brass alloys listed in the table above. FIG. 20 shows the integrated emission intensities (Cu (I) and Zn (I)) for each brass alloy for both approaches. The Zn response curve slopes from LA-LS-APGD and LIBS and are similar, with values of 7819 and 8566, respectively. The Zn response from the microplasma was a factor of 4-5× greater than from the LIBS measurements alone; this was not the case for the Cu emission line as the LIBS signal was more intense than from the laser ablated LS-APGD plasma. Under these conditions, the LIBS measurements did not detect changes in Cu concentrations via the Cu (I) intensities, whereas the laser ablated LS-APGD measurements show a slight increase in response as the copper concentration was increased. The differences in the intensities for the two elements reflect a difference in the excitation conditions (temperatures) between the two plasma environments. Alternatively, this may be an indication that the microplasma is less effective in vaporizing the larger particles than the LIBS plasma. Even so, concentration-dependent responses are observed in the case of microplasma sampling.

Figure 21:
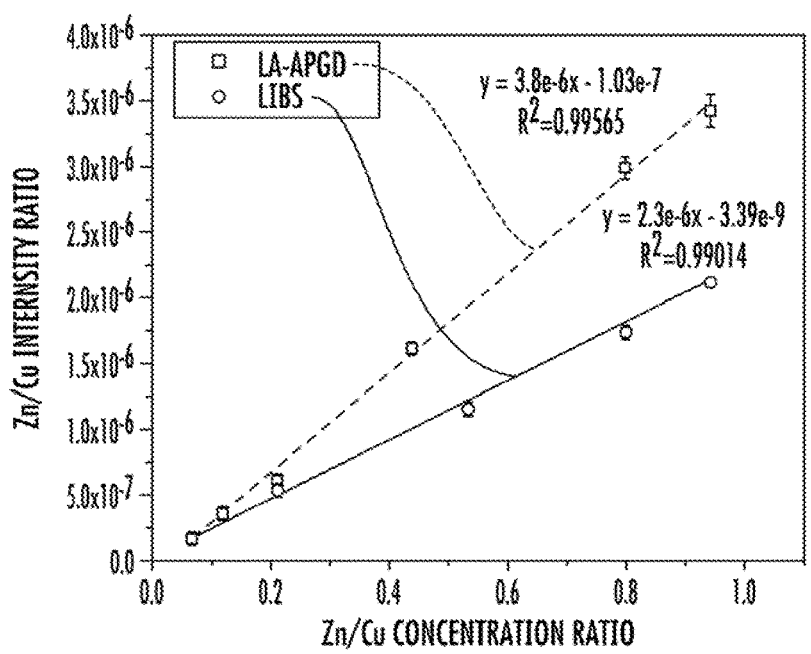
FIG. 21 illustrates Zn (I)/Cu (I) optical emission ratios (obtained from FIG. 20) as a function of elemental concentration for a set of brass standards using LS-APGD and LIBS optical emission spectrometry.

As a final measure of performance, the ability to obtain qualitative response curves from the brass alloys was evaluated. Data in FIG. 20 for Cu and Zn intensities followed similar behavior as previously reported using LA-ICP-MS. As shown in FIG. 21, the Zn (I)/Cu (I) ratio was found to be linear with the elemental composition ratios for both techniques, with good correlation coefficients ($R^2$).

What is claimed is:

1. A liquid sampling, atmospheric pressure, glow discharge (LS-APGD) device comprising:
   an electrolyte solution source;
   a first hollow tube extending from the electrolyte solution source to a first discharge end of the first hollow tube, the first hollow tube comprising a wall surrounding an interior space and further comprising a conductive element, the first hollow tube being in fluid communication with the electrolyte solution source and being configured to carry a flow of a liquid electrolyte solution within the first hollow tube and deliver the electrolyte solution out of the first discharge end;
   a second hollow tube the second hollow tube comprising a wall surrounding an interior space and the second hollow tube including a terminal portion at a second discharge end, the terminal portion comprising a counter electrode, the second discharge end being disposed at a distance of from about 0.1 millimeters to about 5 millimeters from the first discharge end;
   a glow discharge space being external to the first discharge end of the first hollow tube and external to the second discharge end of the second hollow tube and within an electric field established between the conductive element and the counter electrode;
   a power source in electrical communication with the conductive element and the counter electrode, the power source being configured to establish the electric field; and
   an analysis instrument in communication with the glow discharge space.

2. The LS-APGD device of claim 1, further comprising a pump in fluid communication with the electrolyte solution source.

3. The LS-APGD device of claim 1, wherein the first discharge end of the first hollow tube comprises the conductive element.

4. The LS-APGD device of claim 1, wherein the first discharge end of the first hollow tube comprises a non-conductive material, a metal, a polymer, a glass, fused silica, or silicon.

5. The LS-APGD device of claim 1, further comprising a conduit surrounding the first discharge end of the first hollow tube, the conduit defining an annular space surrounding the first discharge end.

6. The LS-APGD device of claim 1, the conductive element extending into the interior space of the first hollow tube.

7. The LS-APGD device of claim 1, wherein the analysis instrument detects optical emission signals in the glow discharge space.

8. The LS-APGD device of claim 1, wherein the analysis instrument comprises a mass spectrometer.

9. The LS-APGD device of claim 8, wherein the mass spectrometer is configured to extract ionic species from the glow discharge space.

10. The LS-APGD device of claim 1, wherein the interior space of the first hollow tube defines an inside diameter of from about 0.1 millimeter to about 2 millimeters.

11. The LS-APGD device of claim 1, wherein the interior space of the second hollow tube defines an inside diameter of from about 0.1 millimeter to about 2 millimeters.

* * * * *